(12) United States Patent
Wijdenes

(10) Patent No.: US 10,030,072 B2
(45) Date of Patent: Jul. 24, 2018

(54) METHOD OF GENERATING ANTIBODIES

(71) Applicant: MAB Design Ltd, London (GB)

(72) Inventor: John Wijdenes, Larnod (FR)

(73) Assignee: MAB DESIGNS LIMITED, London (GB)

( * ) Notice: Subject to any disclaimer, the term of this patent is extended or adjusted under 35 U.S.C. 154(b) by 0 days.

(21) Appl. No.: 14/419,218

(22) PCT Filed: Aug. 2, 2013

(86) PCT No.: PCT/EP2013/066250
§ 371 (c)(1),
(2) Date: Feb. 2, 2015

(87) PCT Pub. No.: WO2014/020139
PCT Pub. Date: Feb. 6, 2014

(65) Prior Publication Data
US 2015/0203582 A1    Jul. 23, 2015

(30) Foreign Application Priority Data

Aug. 3, 2012 (GB) .................................. 1213858.2

(51) Int. Cl.
| | | |
|---|---|---|
| *C07K 16/00* | (2006.01) | |
| *C07K 16/06* | (2006.01) | |
| *C07K 16/30* | (2006.01) | |
| *G01N 33/68* | (2006.01) | |
| *C07K 16/28* | (2006.01) | |

(52) U.S. Cl.
CPC .......... *C07K 16/2866* (2013.01); *C07K 16/00* (2013.01); *C07K 16/005* (2013.01); *C07K 16/06* (2013.01); *C07K 16/30* (2013.01); *G01N 33/6854* (2013.01); *C07K 2317/33* (2013.01); *C07K 2317/34* (2013.01); *C07K 2317/55* (2013.01); *C07K 2317/76* (2013.01); *G01N 2333/7155* (2013.01)

(58) Field of Classification Search
CPC ...... C07K 16/00; C07K 16/005; C07K 16/06; C07K 16/2866; C07K 16/30; C07K 2317/33; C07K 2317/55; C07K 2317/76; C07K 2317/34; G01N 33/6854; G01N 2333/7155
See application file for complete search history.

(56) References Cited

U.S. PATENT DOCUMENTS

| 5,281,699 A | 1/1994 | Chang | |
|---|---|---|---|
| 5,292,867 A | 3/1994 | Chang | |
| 6,274,347 B1 | 8/2001 | Tedder et al. | |
| 7,202,346 B2 * | 4/2007 | Payne | ............... A61K 47/48569 424/134.1 |
| 2005/0142609 A1 * | 6/2005 | Seed | ............ C07K 16/00 435/7.1 |
| 2007/0036809 A1 * | 2/2007 | Michl | ............ A61K 31/675 424/185.1 |

FOREIGN PATENT DOCUMENTS

| WO | WO 95/24913 | 9/1995 |
|---|---|---|
| WO | WO 03/089451 A2 | 10/2003 |
| WO | WO 2005/079508 A2 | 9/2005 |
| WO | WO 2011/023787 | 3/2011 |
| WO | WO 2011/091435 A2 | 7/2011 |

OTHER PUBLICATIONS

Rudikoff et al., Proc. Natl. Acad. Sci. USA 1982 vol. 79 p. 1979.*
Wu et al., J. Mol. Biol. 294: 151-162, 1999.*
International Search Report and Written Opinion of corresponding PCT/EP2013/066250, dated Dec. 5, 2013, 19 pages.
Written Opinion of the IPEA corresponding PCT/EP2013/066250, dated Jun. 26, 2014, 8 pages.
IPRP of corresponding PCT/EP2013/066250, dated Oct. 21, 2014, 23 pages.
Read et al., "Cell-free pool of CD14 mediates activation of transcription factor NF-$_\kappa$B by lipopolysaccharide in human endothelial cells," Proc. Natl. Acad., Sci. USA, vol. 90, pp. 9887-9891, Nov. 1993, XP002713792.
Callahan et al., "Analysis of HIV-Induced Autoantibodies to Cryptic Epitopes on Human CD4", The Journal of Immunology, The American Association of Immunologists, vol. 149, No. 6, Sep. 15, 1992, pp. 2194-2202, XP002964406.
Zijlstra et al., "Targeting the proteome/epitome, implementation of subtractive immunization", Biochemical and Biophysical Research Communications, vol. 303, 2003, pp. 733-744, XP002713793.
Xu et al., "Generation of Monoclonal Antibodies to Cryptic Collagen Sites by Using Subtractive Immunization", Hybridoma, vol. 19, No. 5, 2000, pp. 375-385, XP002428171.
Sleister et al., "Subtractive immunization: a tool for the generation of discriminatory antibodies to proteins of similar sequence", Journal of Immunological Methods, vol. 261, 2002, pp. 213-220, XP004341281.

(Continued)

*Primary Examiner* — Phuong Huynh
(74) *Attorney, Agent, or Firm* — Lewis Roca Rothgerber Christie LLP

(57) ABSTRACT

The present invention discloses a reliable and efficient method of generating an antibody which can discriminate between the membrane bound form of an antigen and the soluble form of the same antigen. Said method comprises the steps of: (i) immunizing an animal with a first antigen which comprises either the membrane bound form or the soluble form of the antigen; (ii) administering to the animal an agent which selectively kills rapidly dividing cells; (iii) when the first antigen of step (i) comprises the soluble form, immunizing the animal with a second antigen which comprises the membrane bound form of the antigen, or when the first antigen of step (i) comprises the membrane bound form, immunizing the animal with a second antigen which comprises the soluble form of the antigen; and (iv) screening for an antibody which can bind to the second antigen but which does not bind to the first antigen.

7 Claims, 7 Drawing Sheets

(56) References Cited

OTHER PUBLICATIONS

Lefebvre et al., "Antigenic differences among porcine circovirus type 2 strains, as demonstrated by the use of monoclonal antibodies", Journal of General Virology, vol. 89, 2008, pp. 177-187, XP002502412.

Agrawal, Babita, et al.; "Expression of MUC1 Mucin on Activated Human T Cells: Implications for a Role of MUC1 in Normal Immune Regulation"; American Association for Cancer Research; Sep. 1998; (58); pp. 4079-4081.

Ackerman, Margaret E. et al.; "Effect of antigen turnover rate and expression level on antibody penetration into tumor spheroids"; Molecular Cancer Therapeutics; 7; 2008; pp. 2233-2240.

Ashraf, SQ et al.; "Humanised IgG1 antibody variants targeting membrane-bound carcinoembryonic antigen by antibody-dependent cellular cytotoxicity and phagocytosis"; British Journal of Cancer; 101; 2009; pp. 1758-1768.

Brooks, Cory L. et al.; "Antibody recognition of a unique tumor-specific glycopeptide antigen"; PNAS; vol. 107; No. 22; Jun. 1, 2010; pp. 10056-10061.

Brooks, Peter C. et al.; "Subtractive Immunization Yields Monoclonal Antibodies that Specifically Inhibit Metastasis"; The Journal of Cell Biology; vol. 122; 1993; pp. 1351-1359.

Carter, Paul et al.; "Identification and validation of cell surface antigens for antibody targeting in oncology"; Endocrine-Related Cancer; 11; 2004; pp. 659-687.

Denisova, Galina et al.; "Characterization of new monoclonal antibodies that discriminate between soluble and membrane CD4 and compete with human anti-CD4 autoimmune sera"; Molecular Immunology; 40; 2003; pp. 231-239.

Hassan, Raffit et al.; "Anti-mesothelia Immunotoxin SSIP in Combination with Gemcitabine Results in Increased Activity against Mesothelin-Expressing Tumor Xenografts"; Clinical Cancer Research; 13; 2007; pp. 7166-7171.

Holbrook, Felicity L. et al.; "Tolerization as a tool for generating novel monoclonal antibodies"; Immunology and Cell Biology; 80; 2002; pp. 319-322.

Junghans, R. P et al.; "Impact of antigenemia on the bioactivity of infused anti-Tac antibody: Implications for dose selection in antibody immunotherapies"; PNAS; vol. 95; Feb. 1998; pp. 1752-1757.

Laferté, Suzanne et al.; "Monoclonal Antibodies Specific for Human Tumor-Associated Antigen 90K/Mac-2 Binding Protein: Tools to Examine Protein Conformation and Function"; Journal of Cellular Biochemistry; 77; 2000; pp. 540-559.

Matthew, William D. et al.; "Cyclophosphamide treatment used to manipulate the immune response for the production of monoclonal antibodies"; Journal of Immunological Methods; 100; 1987; pp. 73-82.

Prinssen, Helena M. et al; "Biodistibution of $^{111}$In-labelled engineered human antibody CTM01 (hCTM01) in ovarian cancer patients: influence of prior administration of unlabelled hCTM01"; Cancer Immunol Immunotherapy; 47; 1998; pp. 39-46.

Rudnick, Stephen I. et al.; "Affinity and Avidity in Antibody-Based Tumor Targeting"; Cancer Biotherapy and Radiopharmaceuticals; vol. 24; No. 2; 2009; pp. 155-160.

Scheefers-Borchel, Ursula et al.; "Discrimination between fibrin and fibrinogen by a monoclonal antibody against a synthetic peptide"; PNAS; vol. 82; Oct. 1985; pp. 7091-7095.

Scott, Andrew M et al.; "Antibody therapy of cancer"; Nature Reviews Cancer; vol. 12; Apr. 2012; pp. 278-287.

Zhang, Yujian et al.; "Immunotoxin and Taxol synergy results from a decrease in shed mesothelin levels in the extracellular space of tumors"; PNAS; vol. 104; No. 43; Oct. 2007; pp. 17099-17104.

Zhang, Yujian et al.; "High Shed Antigen Levels within Tumors: An Additional Barrier to Immunoconjugate Therapy"; Clinical Cancer Research; 14(24); Dec. 2008; pp. 7981-7986.

* cited by examiner

METHOD OF GENERATING ANTIBODIES

CROSS-REFERENCE TO RELATED APPLICATIONS

This application is a National Phase Patent Application and claims priority to and the benefit of International Application Number PCT/EP2013/066250, filed on Aug. 2, 2013, which claims priority to British Patent Application Number 1213858.2, filed on Aug. 3, 2012, the entire contents of all of which are incorporated herein by reference.

This invention relates to a method of generating an antibody which can discriminate between the membrane bound form of an antigen and the soluble form of the antigen. Such antibodies have clear uses in therapeutic and other applications, for example in diagnosis or quality control.

The treatment of human disease using monoclonal antibodies is still at an early stage but is an area that shows great promise. The use of monoclonal antibodies is reserved for disease states in which the target for intervention is both clearly identified and accessible. There are highly successful antibodies on the market for use in transplant, anti-coagulation, anti-inflammatory, autoimmune and cancer therapy. There are many more in development for an even wider spectrum of disease states including multiple sclerosis, allergy, and even drug addiction.

Thus, monoclonal antibodies for the treatment of human disease constitute an exciting new class of therapeutics generating sales in excess of US$16 bn per annum. Antibodies can distinguish their target antigen with exquisite selectivity and are less likely than new chemical entities (NCEs) to demonstrate unacceptable toxicity. Antibody drugs have proven highly successful in the treatment of blood borne cancers but less effective against solid tumours.

In this regard, although there has been some considerable success in the treatment of cancer using antibodies, there have also been a high number of failures. Initial expectations were high, as it was believed that the target antigen could be selected to be present on the cancer cell but not on normal tissue. The selectivity of the antibody should thus ensure that only the cancer cells were treated and the tumour cells were killed in a more selective manner than could be achieved with conventional chemo- or radio-therapies. As mentioned above, for the blood borne cancers or leukaemias, antibody therapy has proven to be significantly effective, but this has not been matched in the treatment of solid tumours, as, with the exception of Herceptin and Avastin, antibody therapies have not proven particularly beneficial.

The lack of efficacy in the treatment of solid tumours may be the result of a number of factors:
a) Solid tumours are dense and poorly vascularised internally. The antibody molecule is large and may simply take too long to penetrate the tumour mass.
b) Tumours are heterogeneous and the antigen target may not be present on the surface of all cells within the tumour mass.
c) Tumour cells shed antigen from the cell surface, the soluble circulating antigen is binding the therapeutic antibody.

Factors a) and b) have been addressed by attaching to the therapeutic antibody a killing agent that acts in a localised but non-discriminatory way. This is referred to as antibody conjugation. These agents include radio-isotopes of elements such as Yttrium, Iodine, Indium or Cobalt. A range of chemotoxic agents have also been targeted in this way, including conventional cytotoxic drugs, toxins such as ricin and calicheamicin and pro-drugs of several forms. The localisation to the tumour of a non-selective killing agent addresses both the issues of penetration and the heterogeneity of the tumour. However, it does not address the issue of shed antigen.

Alternative methods to address factor a) involve the administration of the antibody in very large amounts to try and reach all the cells in the interior of the tumour, but in some cases large amounts of antibody cannot be given because of undesirable side effects. In addition, immunoconjugates comprising a killing agent such as those described above cannot be given in large amounts because of the non-specific side effects of the radio-isotope, drug or toxin. When antibodies are administered at lower doses, it is believed that the shed antigen levels mentioned in factor c) can be high enough to present a significant problem and to interfere with the action of the immunoconjugate.

Studies carried out by the Pastan group (Laboratory of Molecular Biology, NCI Bethesda) have recognised the potential problems associated with shed antigen in the blood and also in the interstitial space of tumours and have made the observation that the concentration of a particular shed tumour antigen, mesothelin, within the tumor and the blood is lowered by chemotherapy. They have suggested that the reduction in the levels of shed antigen by chemotherapy should enhance the efficacy of immunoconjugate therapies (Zhang et al, PNAS, 2007, 104(43): 17099-17104; Zhang and Pastan, Clin Cancer Research 2008: 14(24): 7981-7986). Prinssen et al (Cancer Immunol Immunotherapy, 1998, 47:39-46) also observed a problem with the circulating (shed) antigen MUC1 in ovarian patients in that the administration of a therapeutic radiolabelled antibody directed against the MUC1 antigen was resulting in the formation of radiolabelled immune complexes in the circulation which were then accumulating to problematic levels in the liver. To try and overcome the problem of circulating radioactive immune complexes and their accumulation in the liver, this group came up with the strategy to administer a dose of unlabelled antibody (to mop up the circulating antigen) before they administered the radiolabelled antibody.

The present inventor however has devised a very different way of addressing the problem of shed antigen by developing a method which enables antibodies to be generated which can distinguish between the membrane bound form and the soluble form of the same antigen. This finding is indeed surprising as, to the inventor's knowledge, it has not previously been demonstrated or reported in the literature that it is possible to readily select antibodies that will bind only to the membrane bound antigen and not the soluble form, or vice versa. Such antibodies which for example bind to the membrane bound form of the antigen but not the soluble form would not be decoyed by soluble (shed) antigen in the circulation or in the interstitial spaces of the tumor but would instead target straight to the tumor cell membranes. Such antibodies, which can now be readily identified by the methods described herein, thus provide an alternative and advantageous solution to the problem of shed antigen as well as having many other applications. Although such antibodies may well be useful therapeutically in an unconjugated form, when coupled to killing agents or chemotoxic agents such as those described above and elsewhere herein, such antibodies should significantly overcome all three of the factors identified above. It is also likely that such antibodies (in either a "naked" unconjugated form or coupled to killing agents) will be effective at lower doses, which should result in fewer side effects and a more cost effective treatment.

Although not wishing to be bound by theory, it is believed that the methods of the present invention work due to the fact that the three dimensional conformation (tertiary structure) of most proteins is different when they are anchored to or associated with a membrane (are membrane bound) to the conformation they adopt in the soluble or aqueous phase (soluble form). Although such changes are often very subtle and may in fact have no bearing on the function of the protein, the findings of the present invention demonstrate that such changes can be recognised by antibodies and, moreover, a technique to reliably generate such antibodies which can discriminate between the membrane bound and soluble forms of an antigen has been developed. These findings were surprising given the closely related nature of the soluble and membrane bound forms of the same antigen.

The method for preparation of an antibody which will bind only to a membrane bound antigen and not one in the soluble phase (or vice versa), i.e. an antibody which can discriminate between the membrane bound and soluble form of an antigen is necessarily more complex than the preparation of a conventional antibody. However, the combination of steps as described herein, which involve for example the induction of tolerance combined with whole cell immunization, have been shown in the present application to be particularly effective in generating such antibodies.

At its most general, the present invention provides a method of generating an antibody which can discriminate between the membrane bound form of an antigen and the soluble form of the antigen, comprising:

(i) immunizing an animal with a first antigen which comprises either the membrane bound form or the soluble form of the antigen;

(ii) administering to the animal an agent which selectively kills rapidly dividing cells;

(iii) when the first antigen of step (i) comprises the soluble form, immunizing the animal with a second antigen which comprises the membrane bound form of the antigen, or when the first antigen of step (i) comprises the membrane bound form, immunizing the animal with a second antigen which comprises the soluble form of the antigen; and (iv) screening for an antibody which can bind to the second antigen but which does not bind to the first antigen.

Unless otherwise described herein, the method steps of the invention are generally carried out in the order presented above, although additional steps may be present and some steps may be repeated.

The term "immunization" or "immunizing" or "immunized" and equivalent terms as used herein refer to a step in which an animal is exposed to a foreign molecule (e.g. an antigen) in such a way which causes the immune system of the animal to generate an immune response against the foreign molecule. Such exposure to an antigen is carried out in a controlled way (active immunization) for example by injecting or otherwise administering the antigen to the animal or bringing the animal into contact with the antigen. The amount of antigen administered in such an immunization step thus has to be sufficient to stimulate an immune response in the animal. Appropriate adjuvants will generally be used unless the antigen alone can act as an immunogen and can itself stimulate an appropriate immune response.

The animal to be used in the methods of the present invention can be any animal which is capable of mounting an immune response to the antigen of interest. Preferred animals are thus non-human animals or mammals. Any livestock, domestic or laboratory animal can be used. Specific examples include rodents (e.g. rats, mice, guinea pigs, hamsters), ferrets, rabbits, llamas, sheep, pigs, cows, dogs, cats and non-human primates.

More preferred animals for use in the methods of the present invention are mice and llamas, particularly mice.

The methods of the invention are used to generate useful antibodies. Although the antibodies generated by such methods will have therapeutic and diagnostic applications, the methods of the invention are not themselves designed to be carried out as methods of treatment of the animal body by surgery or therapy or as diagnostic methods practiced on the animal body. The methods can therefore be viewed as experimental or non-therapeutic methods, for example carried out on test animals, e.g. experimental or laboratory animals, and are designed to generate useful antibodies. The methods of the invention which generate antibodies are not themselves designed to have a therapeutic effect or therapeutic benefit on the animal on which they are carried out.

For the present invention to work it is important that the presence of the first or second antigen in the animal by way of the immunization steps results in the rapid proliferation, activation, division or amplification of B cells (B lymphocytes) that produce an antibody to that particular antigen. Such proliferation, etc., of B cells would occur in a natural immune response to an antigen to which the animal had been exposed and thus the methods of the present invention harness this natural response. However, following the administration of the first antigen in order to stimulate proliferation of the relevant B cells (step (i) of the method), the animal is treated with an agent which selectively kills rapidly dividing cells (step (ii) of the method). This has the effect that the B cells which are producing antibodies to that first antigen (in that conformation) and therefore are rapidly dividing, are depleted from the system. Once these B cells have been depleted the animal is then contacted with (immunized with) a second antigen (step (iii) of the method), which comprises the other form of the antigen (membrane bound or soluble) to the form used in step (i). In this step, the only B cells which are stimulated to replicate (or at least a significant proportion of the B cells which are stimulated to replicate) will be those that recognise the difference in conformation between the first and second antigen as they did not themselves recognise the form of the first antigen but they recognise the second antigen. In this way B cells producing antibodies which discriminate between the membrane bound and soluble form of an antigen are produced and antibodies which can bind to the membrane bound form but not the soluble form (or vice versa) can be generated.

In the methods of the present invention, the first antigen can be either the membrane bound form of the antigen or the soluble form of the same antigen, and is selected depending on which population of B cells it is wished to deplete. Thus, if it is desired that the antibody generated by the method should be able to bind to the membrane bound form of the antigen but not the soluble form, then the first antigen will be the soluble form, and vice versa. Thus, the first antigen can be viewed as the "non-target antigen" (i.e. the form of the antigen which it is desired that the antibodies do not bind) and the second antigen as the "target antigen" (i.e. the form of the antigen to which it is desired that the antibodies bind).

In preferred embodiments of the invention, the first antigen is the soluble form and the second antigen, to which it is desired that antibodies are generated which can discriminate from the first antigen, is the membrane bound form. In such embodiments, it is further preferred that the antibodies which can bind to the membrane bound form but not the soluble form of the antigen will dissociate from the membrane bound form if it ceases to be bound to the membrane.

In alternative embodiments, it is equally possible that the first antigen is the membrane bound form and the second antigen is the soluble form.

The first two steps of the method (steps (i) and (ii)) are similar to the way in which tolerance is induced in an animal and are thus sometimes referred to herein as tolerance steps or tolerance immunization. The present inventor has shown that by creating tolerance to the first antigen (e.g. the soluble form of a particular antigen) the immune response can be developed against the second antigen (e.g. the membrane bound form of the same particular antigen). This finding was in fact surprising given the fact that the same antigen is used for both the tolerance steps (i) and (ii) and the immunization step (iii). In this regard, it was surprising and counter-intuitive that a method which involves a step in which the B cells which respond to the antigen you are trying to make antibodies against are depleted in steps (i) and (ii), can form part of a reliable method to generate antibodies to the same antigen when this is used to immunize the animal in step (iii).

Antigens for use in the present invention can comprise or consist of any molecules which can be recognised as foreign by the immune system of the animal used and which will result in an immune response being initiated and the production of antibodies. The antigen chosen for use in the present invention will be any antigen which has distinct membrane and soluble forms (for example forms which show some kind of difference in 3-dimensional or tertiary structure), and where it is desired that an antibody be generated which can distinguish between the two forms. This difference between the membrane bound and soluble forms can be very small, for example can be any change in conformation, as it is believed that the sensitivity of the method means that antibodies can be generated which will discriminate between antigens with only minor differences in conformation.

For example, the present inventor has found (data not shown) that this method can be used to generate antibodies which can distinguish between molecules which differ by only three amino acids in length and which specifically bind the shorter form. Such antibodies must be recognising a different conformation as there are no unique amino acid sequences to bind to.

The difference in conformation must be such that it can be specifically recognised by an antibody, i.e. an antibody will recognise and be able to bind to an epitope on one form but not the other, the surprising fact being that the present invention allows antibodies to readily be generated which are capable of distinguishing between two such closely related antigens in the form of membrane bound and soluble forms of the same antigen (i.e. antigens which will generally be closely related in terms of sequence, for example have at least 80%, 85%, 90%, 95%, 98% or 99% identity at the amino acid level, and in some cases will have essentially identical or identical sequences). Exemplary antigens which may have closely related sequences but different conformations would include antigens which differ by one or more point mutations or by a short amino acid insertion or deletion (e.g. of up to 10 amino acids, for example up to 3 or 5 or 7 amino acids or antigens which are no longer attached to a membrane due to for example the removal of the external membrane domain or another component which serves to link the antigen to the membrane, e.g. a glycophosphatidyl inositol linkage). Such antigens will thus include truncated molecules or fragments or shorter forms of longer antigens, for example cleavage products or splice variants, or isoforms. The soluble form of antigen may thus be derived from the membrane bound form, for example by cleavage, or may simply exist independently.

It can be noted that there is no requirement in the methods of the invention for the precise differences in the membrane and soluble forms of the antigen to have been characterised. It is sufficient to know that the two different forms exist and to know or suspect that they have a difference in conformation. If they do indeed have a difference in conformation then the methods of the invention should allow discriminatory antibodies to be generated.

Thus, preferred antigens will be tumour associated antigens which are expressed on tumour cells (membrane bound form) and also shed from the tumour, e.g. into the circulation or interstitial space of the tumour (soluble form, also referred to herein as "shed antigen"). The vast majority of tumour associated antigens are subject to such shedding and thus any of these would be appropriate for use in the present invention providing the two forms were different in conformation. Indeed, as outlined above, preferred tumour associated antigens are those associated with solid tumours. However, it is important to appreciate that the methods used mean that the present invention is not confined to generating antibodies to tumour associated antigens. Indeed, virtually all structural and functional categories of membrane proteins have been found to be shed from cells. Thus, although the methods of the present invention have been exemplified using soluble and membrane bound GP80 and mesothelin, the methods are generally applicable to any antigens with a distinct membrane bound and soluble form.

As indicated above, there are many examples of antigens which have a distinct membrane and soluble form and the invention is not limited to any particular antigen. However, purely by way of example, other preferred antigens might be CD125, CD130, TRAIL receptors, CD25, CD69 and many others.

Preferred antigens are human antigens but other mammalian antigens can equally be used, especially where the generation of antibodies which cross react with the same antigen from different species is desired. Thus, in such embodiments the method of the invention can be carried out using for example a human antigen, but is then also carried out with one or more of the equivalent antigens from other mammalian species, e.g. also with mouse antigen or rat antigen or primate antigen.

The membrane bound form of an antigen refers to an entity which is attached to, associated with, embedded in, or otherwise bound to a cell membrane, or is a component of a cell membrane, for example can be referred to as a cell surface antigen or a cell surface molecule. Such membrane bound forms will thus in many cases represent the native forms of the antigen. Although antigens will often be protein containing molecules (polypeptides or glycoproteins) it is equally possible that the methods of the invention can be used to generate antibodies against other types of membrane bound entity, such as entities comprising or consisting of carbohydrate (e.g. polysaccharides) or lipid (e.g. phospholipid) entities. Preferred membrane bound form antigens are tumour associated antigens, in particular antigens associated with solid tumours, or antigens associated with sub-types of T-cells.

The soluble form of an antigen refers to an entity which is present in solution or in a soluble phase. Thus, this form of the antigen is not associated with a membrane and is not particulate and not in the form of an insoluble aggregate or precipitate. A preferred form of soluble antigen is an antigen which was associated with the surface of a cell, e.g. a disease associated cell such as a tumour cell, and has been shed or lost from the cell membrane to become a soluble antigen, for example by cleavage (such antigens are also referred to herein as "shed" antigens). The soluble antigen can also be synthesised in the cytoplasm and secreted by endocytosis and/or other mechanisms. Such shed antigens are often found in the blood but are also found in the interstitial space of tissues, for example in the interstitial space of tumors.

In the methods of the invention, the membrane bound form of the antigen used for immunization can be provided from any appropriate source, e.g. can be provided in the form of any appropriate membrane containing sample or preparation. For example, the animal can be immunised with a whole cell preparation wherein the cells have on their surface the appropriate antigen. Preferably the cells used for immunization will overexpress the membrane bound form of the antigen, e.g. the cells may take the form of tumour cells or cells from a different disease state which are known to overexpress the antigen of interest.

Alternatively, cells can be engineered to express or overexpress the antigen of interest using appropriate recombinant techniques, for example by transfecting the cells with an expression vector designed to overexpress the antigen of interest. When the antigen of interest is overexpressed it is preferred that the cell line used for overexpression is a cell line unrelated to the disease in question. Thus, preferred cell lines are generally mammalian host cells such as CHO, P815 PER.C6, HeLa, BAF3 or COS cells for which methods of transfection are well established and in which the antigen of interest will be the major protein that is expressed on the cell surface. In some embodiments it is preferred that the cell line used for immunization will be matched to the animal being used in the methods, e.g. a murine cell line is sometimes preferred when the methods are carried out in mice.

It is equally possible in the methods of the present invention to use membrane preparations as opposed to whole cell preparations in the immunization step with the membrane bound form of the antigen. Appropriate membrane preparations are available commercially or can be readily prepared by methods well known and described in the art.

The soluble antigen used for immunization can be provided from any appropriate source, i.e. any sample or source in which the desired antigen is present in a soluble form. In the case of antigen shed from a tumour (or indeed any soluble antigen shed from a cell into the circulation) then an appropriate source might be blood from a relevant subject (e.g. patients that are afflicted with the tumour or otherwise contain the cells in question from which the antigens are shed). Equally, normal serum, e.g. normal human serum, would be an appropriate source for certain soluble antigens which exist in normal serum. Whole blood or serum could be used or equally the antigen could be wholly or partially purified from the blood or serum (or indeed any appropriate source), e.g. using appropriate antibodies, before using in the methods of the invention.

Another source of soluble antigen where shed antigens are concerned would be to carry out in vitro cultures of relevant cells which have the membrane bound form of the antigen and to use the culture medium as a source of the shed antigen. For example, the soluble form of the antigen could be produced by utilizing recombinant methods as outlined above, where cells can be engineered to express or overexpress the membrane bound form of the antigen of interest using appropriate recombinant techniques, for example by transfecting the cells with an expression vector designed to overexpress the antigen of interest. In such systems, whilst overexpression of the membrane bound form of the antigen will occur, equally, as shedding is a natural process, relevant soluble forms of the antigen will be shed into the culture medium which can then be used as a further source for the soluble form of the antigen. If necessary, appropriate proteases could be used to increase the amount of shed antigen.

Alternative recombinant techniques can be used to produce the soluble antigen including for example expressing the antigen in question without a transmembrane domain in a host cell in order that it would be secreted into the culture medium.

If the desired soluble antigen is located in the interstitial spaces of tissues or tumours then such tissues or tumours provide further sources.

Certain soluble antigens will be commercially available. A preferred source of soluble antigen for immunization in the methods of the invention would be blood/serum, e.g. human serum and/or the supernatant of cells. Preferred antigens for use in the methods of the present invention are human antigens but (as discussed above) does not exclude other mammalian antigens and in such embodiments sources are chosen appropriately. Preferably in the methods of the invention a single soluble antigen is administered, conveniently in a purified form.

Step (ii) of the method of the invention involves the administration of an agent which selectively kills rapidly replicating cells. In this case the target cells are B cells which have been stimulated to divide by exposure to the first antigen. Although the target cell population is B cells, as this cell type will be one of the only cell types which is actively proliferating, then it is not required that the agent has to specifically recognise B cells; it is sufficient that the agent is selective for any rapidly dividing population of cells, as this will ensure that the relevant B cell population is killed, i.e. the B cell population that is recognizing and proliferating in response to the administration of the first antigen.

Appropriate agents which are capable of selectively killing rapidly replicating/dividing cells would be well known to a person skilled in the art and any appropriate agent could be used. Generally, any cytostatic or cytotoxic compound or drug could be used, for example cyclophosphamide, or indeed any other drugs used in chemotherapy which have as their mode of action the prevention of cell growth or the killing of rapidly dividing cells.

As mentioned above, agents which selectively kill or target rapidly dividing or replicating cells are well known in the art. For example, the most common chemotherapy agents act by killing or damaging cells that divide rapidly, as this is one of the main properties of most cancer cells. This means that chemotherapy also harms cells that divide rapidly under normal circumstances, e.g. cells in the bone marrow, digestive tract, and hair follicles. This effect on other (non cancerous) cells is harnessed in the present invention where it is desired that actively replicating B cells are killed. Said agents generally act by impairing mitosis (cell division), thus in effect being selective for or targeting rapidly dividing cells. Such agents are also described as cytotoxic or cytostatic agents.

Appropriate chemotherapeutic agents for use in the methods of the present invention would be readily apparent to a person skilled in the art and would include drugs which affect cell division or DNA synthesis or function in some way. Exemplary chemotherapeutic agents are alkylating agents (e.g. cisplatin, carboplatin, oxaliplatin) or other agents which work by chemically modifying DNA such as mechlorethamine, cyclophosphamide, chlorambucil and ifosfamide; antimetabolites; anthracyclines; plant alkaloids (e.g. vinca alkaloids and taxanes such as paclitaxel (Taxol) and docetaxel); topoisomerase inhibitors (e.g. type I topoisomerase inhibitors such as camptothecins, e.g. irinotecan and topotecan, or type II topoisomerase inhibitors such as amsacrine, etoposide, etoposide phosphate, and teniposide); or cytotoxic antibiotics. A preferred agent is cyclophosphamide.

If necessary, there are a number of cytotoxicity assays which can be used by a person skilled in the art to assess whether or not an agent has the capability of selectively killing rapidly dividing cells and any of these can be used to assess whether or not an agent is appropriate for use in the methods of the invention. Merely as an example, assessing cell membrane integrity is one of the most common ways to measure cell viability and cytotoxic effects, as compounds that have cytotoxic effects often compromise cell membrane integrity. Vital dyes, such as trypan blue or propidium iodide are normally excluded from the inside of healthy cells; however, if the cell membrane has been compromised, they freely cross the membrane and stain intracellular components and this can readily be assayed in an appropriate cell type. Alternatively, membrane integrity can be assessed by monitoring the passage of substances that are normally sequestered inside cells to the outside. One commonly measured molecule is lactate dehydrogenase (LDH).

The appropriate dose of agent for use in step (ii) of the method and the appropriate timing of administration can readily be determined by a person skilled in the art using their normal skill and routine experimentation. The dose of agent is selected such that it is high enough to be able to exert its cytotoxic effect on B cells but is not so high as to cause unacceptable toxicity or side effects to the animal. Many of the above agents have been approved for administration to humans and so determining appropriate doses for other animals would be routine to a person skilled in the art and guidance will be available in the literature as to appropriate doses and relevant adjustment in case of toxicity. For other agents routine trial and error could readily be used to determine the appropriate doses. Generally, the dose is adjusted for the animal's body surface area, a measure that correlates with blood volume. In the exemplified methods, cyclophosphamide is used at a dose of 1 mg per mouse, which is administered in any appropriate volume but conveniently in a volume of 200 microliters. A 1 mg dose is generally reported in the literature to be appropriate for a mouse. A 10 mg dose may be lethal so doses below 10 mg will generally be used, for example a dose of between 1 mg and 9 mg or between 1 mg and 2 or 5 mgs. Lower doses can be used, for example 500 micrograms or 750 micrograms, if such doses are high enough to be able to exert its cytotoxic effect on B cells but is not so high as to cause unacceptable toxicity or side effects to the animal.

The agent which selectively kills rapidly replicating cells is preferably administered at a time point after the administration of the first antigen such that the B cells of the animal are actively proliferating in response to the first antigen. Such a time point could readily be determined by a person skilled in the art for a particular first antigen and a particular animal model. For example, it is readily possible to test a blood sample of the animal to assess the titre of antibodies being produced against the first antigen and use this information to determine an appropriate time point to administer the killing agent. In general, however, the killing agent would be administered within the first hour after the administration of the first antigen, for example within 15, 20, 30, 45 or 60 minutes. Protocols in which the agent is administered 10 minutes after the first antigen are exemplified herein but other administration regimes could equally be used providing that the B cells are still in a phase of active proliferation when the killing agent is administered.

In order to ensure that sufficient and preferably all or substantially all of the relevant B cells are killed, multiple administrations (e.g. daily administrations) of the killing agent (i.e. at least one administration of the killing agent) are often appropriate. The number and frequency of administrations will depend on the particular agent, the selected dose and the type of animal being subjected to the method. Administration daily for up to 5 days (e.g. for 1, 2, 3, 4 or 5 days or at least 1, 2, 3, 4 or 5 days) is contemplated. For example, in the exemplified protocols the killing agent is administered on the same day as the first antigen and then daily for two further days beyond the day that the first antigen is administered. In practice, a regime involving a first administration at around 15 minutes after the administration of the first antigen, e.g. after 10, 15 or 20 minutes, followed by two subsequent injections at day 1 (around 24 hours) and day 2 (around 48 hours) is likely to work in most cases.

As with any immunization protocol, multiple administrations of the first (and second) antigens are generally desirable in order to stimulate a strong immune response and good B cell replication in response to the antigen. The appropriate number of immunizations can be determined by a person skilled in the art (again for example aided by blood tests on the animal to determine the titre of the relevant antibodies) but generally at least 1, 2, 3, 4 or 5 administrations, for example between 1 and 7, more preferably between 1 and 5 or 1 and 4, and more preferably between 2 and 5 or 2 and 4 or 2 and 6, or between 3 and 5 or 3 and 4 or 3 and 6, or between 4 and 5 immunizations can be used. If multiple administrations of the first or second antigen are used then these can be spaced appropriately, for example every 1, 2 or 3 weeks apart (in the exemplified protocol the administrations are spaced two weeks apart).

If multiple administrations (immunizations) of the first antigen are used, then, in a preferred embodiment of the invention each administration of the first antigen is followed by the step of administration of a killing agent (which, as mentioned above, can involve multiple administrations). Thus, steps (i) and (ii) of the method are preferably repeated one or more times (e.g. repeated at least 1, 2, 3, 4 or 5 times) in order to ensure that as many B cells as possible which recognise the first (unwanted) antigen are depleted from the animal. In the exemplified protocols steps (i) and (ii) are carried out and then repeated 3 times (i.e. in total steps (i) and (ii) are carried out 4 times). However, it will be appreciated that this number can vary depending on the antigen and the animal model and depending on the dose of antigen which is administered. Exemplary numbers are as outlined above for the number of immunizations. The number may even vary from protocol to protocol, particularly if the protocol is being optimized. If desired, the effect of repeating the steps (i) and (ii) could be monitored. For example, titres of antibody against the first antigen could be measured in blood samples taken from the animal after each round of treatment to monitor for the timepoint when there was no longer any reaction, or a very limited reaction, or no further significant reduction in the reaction, against the first antigen. Thus, steps (i) and (ii) are repeated until a significant proportion (e.g. more than 50%, 60%, 70%, 80%, 90% or 95%) of the B cells which recognise the first antigen have been removed. Preferably, all or substantially all B cells which recognise the first antigen are killed. In other words, if measured, the numbers of B cells which could bind to the first antigen would be a minority population and preferably undetectable.

In addition, in some situations, additional tolerization steps can be included in the methods using for example a different first antigen. Thus, for example in some protocols it might be beneficial to carry out an additional tolerization step (i) and (ii) with one or more other undesired antigens. For example, in the case where it is desired to generate an antibody which recognizes the membrane bound form of an antigen, an additional step (i) (and step (ii)) of immunizing (and tolerization) of the animal with a cell type which did not express the antigen of interest (e.g. an untransfected cell line) can be advantageous in order to remove B cells which recognise further unwanted antigens on the cell surface.

The dose of the first and second antigens to be administered can readily be determined and are selected so as to induce a good immune response in the animal and good proliferation of B cells in response to the relevant antigen. The appropriate doses can be determined by trial and error if necessary (or by monitoring the titre of the antibodies being produced as mentioned elsewhere herein). Appropriate adjuvants will be used where necessary. The generation of a good immune response to an antigen can readily be monitored, for example by measuring the titre of antibodies being produced against the antigen in question, e.g. by testing serum from an immunized animal on a cell line expressing the antigen versus a cell line not expressing the antigen, e.g. to look for significant amounts of relevant antibodies to the antigen present in the serum from immunised animals compared to non-immunized animals. In addition, the quality of the immune response can be monitored by assessing the isotypes of the antibodies produced. For example if most immunoglobulins detected are IgG then this is generally a sign of a good quality immunization.

The appropriate dose may also depend on the format of the antigen in question. For example, in embodiments where the soluble form of the antigen is a purified or recombinant molecule then the dose can be determined in the form of μg per animal. Exemplified herein for soluble GP80 or soluble mesothelin is a dose of 1 or 10 μg/mouse, which would be a quite standard dose. When administering the membrane bound form of the antigen then the dose can be determined in the form of number of cells per animal. Appropriate doses could readily be determined. Exemplified herein for JV1 cells or P815 cells is a dose of 1 million or 10 million cells per mouse. Administration can be by any appropriate route, for example intraperitoneal or intravenous administration. For example, in embodiments of the invention where the screening steps involve obtaining B cell populations from the lymph nodes of the animal, the antigen is preferably administered at a dose of 1 μg or 1 million (M) cells, by injection into the foot pad. In embodiments of the invention where the screening steps involve obtaining B cell populations from the spleen of the animal, the antigen is preferably administered at a dose of 10 μg or 10 million (M) cells, by IP injection.

After carrying out step (iii) of the method the B cells which are stimulated to replicate should be highly enriched for those which produce antibodies which recognise the second antigen. Importantly, and in addition, due to the depletion of B cells which produce antibodies which recognise the first antigen in steps (i) and (ii) of the method, the B cells present after step (iii) of the method should also be enriched for those antibodies which recognise the second antigen but do not recognise the first antigen, i.e. should be enriched for B cells producing antibodies which can discriminate between the first and second antigens, i.e. antibodies which can recognise a distinction or difference between a membrane bound form and a soluble form of the antigen. Such antibodies which discriminate are those which can bind to the second antigen but not bind to the first antigen.

A typical and preferred immunization protocol in accordance with the present invention is described in the attached Examples and this protocol can be used and, if necessary, modified as appropriate for different antigens.

The step of screening the candidate antibodies which are present at the end of step (iii) of the method for antibodies which can bind to the second antigen but not to the first antigen (or the step of screening for an antibody which can discriminate between the membrane bound form of an antigen and the soluble form of the antigen) can be carried out by any appropriate assay which could routinely be devised by a skilled person.

However, before such screening takes place it is generally preferred that candidate antibodies from the animal are obtained in a more useful format for screening by appropriate methods. As the candidate antibodies are being produced by the B cells of the animal, the first step will generally be to harvest or otherwise obtain the B cell populations from the animal. Any source of B cells in the animal could be used, for example one or more of the spleen, lymph nodes, bone marrow, peripheral blood, are all appropriate sources.

In a preferred embodiment the B cell populations are obtained and then hybridomas are made from these B cells by methods which are well known and standard in the art.

Hybridoma technology is a standard technique which is used in the art to generate monoclonal antibodies. The techniques are based on the original method invented by Köhler and Milstein (Nature, 1975, 256:495-497, see also Gay et al., 1981, Methods Enzymol. 73, 3-46). Although any appropriate technique may be used, said methods generally involve the fusion of a specific antibody producing B cell with a myeloma cell (B cell cancer) that is selected for its ability to grow in tissue culture and for an absence of antibody chain synthesis. The first stage in generating a hybridoma is the exposure of laboratory animals (mammals, e.g. mice) to an antigen of interest, usually by a series of injections of the antigen in question, over the course of several weeks. This first stage takes place in step (iii) of the method of the present invention. Splenocytes are then isolated from the mammal's spleen (or another appropriate source of B cells is used, e.g. lymph nodes), after which the B cells are fused with immortalized myeloma cells (e.g. NSO myeloma cells). The myeloma cells are selected beforehand to ensure they are not secreting antibody themselves and that they lack the hypoxanthine-guanine phosphoribosyltransferase (HGPRT) gene, making them sensitive to the HAT medium (see below). The fusion is generally accomplished using polyethylene glycol or the Sendai virus to make the cell membranes more permeable.

Fused cells are incubated in HAT medium (hypoxanthine-aminopterin-thymidine medium) for roughly 10 to 14 days. Aminopterin blocks the pathway that allows for nucleotide synthesis. Hence, unfused myeloma cells die, as they cannot produce nucleotides by the de novo or salvage pathways because they lack HGPRT. Removal of the unfused myeloma cells is usually necessary because they have the potential to outgrow other cells, especially weakly established hybridomas. Unfused B cells die as they have a short life span. In this way, only the B cell-myeloma hybrids survive, since the HGPRT gene coming from the B cells is functional. These cells produce antibodies (a property of B cells) and are immortal (a property of myeloma cells). The incubated medium is then diluted into multi-well plates to such an extent that each well contains only one cell. Since the antibodies in a well are produced by the same B cell, they will be directed towards the same epitope, and are thus monoclonal antibodies.

The hybridoma culture supernatant can then be screened to identify only those hybridomas that produce antibodies of appropriate specificity. Hybridomas can be maintained in culture and cryopreserved to ensure that antibodies of interest can be produced indefinitely.

Alternatively and equally preferably to the making of hybridomas, the genetic material can be extracted from the B cell populations (for example by using the spleen cells or lymph nodes of the immunized animal) and used to create antibody expression libraries for use in screening for antibodies of interest. Preferably in this regard, a phage display antibody library would be constructed and screened by methods which are well known and standard in the art. Alternatively, soluble expression systems could be used to express the antibody library and to screen for antibodies of interest.

For example, such methods generally involve the isolation of RNA from an appropriate population of antibody producing cells (B cells) from the immunized animal, e.g. from spleen cells of the immunized animal, after which cDNA can be synthesised from the RNA by appropriate methods, for example using RT-PCR with appropriate primers. Kits are commercially available for both RNA and cDNA preparation and these can conveniently be used. To make the antibody library, sequences encoding the heavy chain and light chain antibody sequences are generated. Again, this can be done using well described methods, for example it can conveniently be done by carrying out PCR using appropriate primers which bind to the 5' and 3' ends of the heavy chain and light chain antibody sequences to form heavy and light chain libraries. Such primers can be readily designed based on known and publically available immunoglobulin gene sequence database information.

The heavy and light chain antibody libraries can then be cloned into appropriate expression vectors to generate an expression library which can be screened. Appropriate expression vectors are well known in the art and can be selected depending on the type of expression library required. For example, phage display vectors are available for phage display selection or other types of vector are available for soluble expression. Appropriate vectors can also be selected depending on the format of antibody to be screened, e.g. whether the antibody library is a Fab library or an scFv library. Appropriate expression systems and techniques, e.g. phage display systems, which are again widely available and well known in the art, are then used for screening of the generated antibody libraries.

Exemplary and highly effective methods of antibody generation and phage display screening are outlined in the Examples.

Once candidate antibodies have been obtained (e.g. in the form of hybridomas or phage display libraries) they can then be screened for antibodies which can bind to the second antigen but not the first antigen (i.e. for antibodies which can discriminate between the membrane bound form of an antigen and the soluble form of the antigen). The meaning of an antibody which can bind to the second antigen but which does not bind to the first antigen would be readily recognized by a person skilled in the art. For example, this term refers to an antibody which shows measurable and preferably significant binding to the second antigen but a low level and preferably an insignificant or undetectable level of binding to the first antigen. Methods by which such screening could be done would be readily apparent to a person skilled in the art. In addition, it should be noted that the method steps (i) to (iii) will have advantageously ensured that the population of B cells obtained from the animal will already have been enriched for antibodies which have these properties. This is clearly demonstrated in the Examples where a significant proportion of the candidate antibodies tested show the ability to discriminate between the membrane bound form and the soluble form of the antigen as opposed to recognizing both the membrane bound form and the soluble form of the antigen. Phage display screening has proved particularly effective and has the advantages of being high throughput and allowing the screening of libraries with increased diversity due to the many combinations of heavy and light chains produced when the antibody libraries are made from the B cell genetic material. As such libraries are formed of DNA, a further advantage is that they are robust and stable.

A convenient way of carrying out the screening for antibodies which can bind to the second antigen but not the first antigen will be the use of some kind of competition assay. Thus, taking the embodiment where the first antigen is the soluble form of the antigen and the second antigen is the membrane bound form, an assay can be used where a sample of the soluble antigen is introduced in order to assess whether such antigen has the ability to compete for the binding of a candidate antibody to a source of the membrane bound form of the antigen. If the soluble antigen can compete to a significant extent then this is indicative that the antibody candidate is not specific for the membrane bound form (as it also binds the soluble form). If the soluble antigen cannot compete to a significant extent then this is indicative that the antibody candidate has the ability to discriminate between the membrane bound and soluble forms.

Thus, by way of example, in an appropriate competition assay, a candidate antibody is regarded as discriminatory if the ability of said antibody to bind to the second antigen is not significantly effected/competed by the addition of said first antigen, e.g. the reduction in binding is less than 2 fold, 1.8 fold, 1.6 fold, 1.4 fold, 1.2 fold or around 1.0 fold, i.e. that there is no significant reduction in binding. In such assays, the first antigen is added at an appropriate concentration (or range of concentrations) such that significant competition would occur if the candidate antibody had the ability to bind to both the membrane bound and soluble form of the antigen.

A convenient way to do this screening would be to carry out FACS analysis using cells which are known to be positive for the membrane bound antigen of interest. In such an assay a significantly reduced signal when the soluble form of the antigen is added indicates that the candidate antibody binds to both the membrane and soluble forms, i.e. does not discriminate, whereas a largely or significantly maintained signal when the soluble form is added indicates that the candidate antibody does not bind the soluble form but does bind the membrane bound form (or there would be no positive signal), i.e. that the antibody can distinguish between the two forms of antigen. Such methods of screening are exemplified herein.

Although FACS analysis is convenient because of the instant and readily quantifiable fluorescent readout, other forms of assay could equally be used to screen for an antibody which can bind to the second antigen but not the first antigen (i.e. for antibodies which can discriminate between the membrane bound form of an antigen and the soluble form of the antigen), such as ELISA or immunofluorescence. For example, in an ELISA assay, a sample of the membrane bound form of the antigen could be coated onto an ELISA plate (e.g. appropriate cells or membrane fractions thereof could be coated onto as ELISA plate) and a similar competition assay carried out using a sample of soluble antigen and the candidate antibodies.

The use of competition assays are of course not required as it would readily be possible to use assays such as ELISA assays to compare the binding of a candidate to a soluble form and a membrane bound form of an antigen by having the two forms of the antigen coated on separate ELISA plates and measuring and comparing the amount of antibody which became bound.

In embodiments where the first antigen is the soluble form and the second antigen is the membrane bound form, then a preferred method of screening is by FACS. In embodiments where the first antigen is the membrane bound form and the second antigen is the soluble form then ELISA (to screen for soluble form binders) against FACS screening (to screen for membrane binders) would be preferred.

It may also in some cases be desirable to carry out an initial round of screening using the second antigen alone in order to select only the candidates which bind the antigen of interest (the target antigen, the second antigen) and thus eliminate any antibodies which do not show this binding. The positive clones can then be subject to further screening to assess whether or not they also do not have the ability to bind the first antigen, i.e. have the ability to discriminate between the membrane bound and soluble forms of the antigen. Again any appropriate method, e.g. FACS (if the second antigen is a membrane antigen) or ELISA can be used.

Where the second antigen is a membrane bound form of the antigen, this initial round of screening can conveniently be carried out by selecting antibodies which bind to a cell expressing the antigen of interest. Optionally, antibodies which bind to such a cell line but which do not bind to a non-expressing cell line (e.g. a non-transfected cell line) are selected. This process can have the effect of enriching the selected population for antibodies which recognise the antigen of interest. This initial round of screening can be carried out with the cell used for immunization but is preferably carried out with a different cell type expressing (e.g. by transfection) the antigen of interest.

Optionally more than one of these initial rounds of screening can be carried out, for example, 2, 3 or even more rounds, preferably on different cell types expressing (e.g. by transfection) the antigen of interest. Such multiple rounds are particularly suited to the screening of phage display libraries. For example, the antibodies selected from the first round could be screened again on a different cell type expressing the antigen of interest in order to further enrich the population of antibodies for those which recognise the antigen of interest. Where 2 (or more) rounds are used it would generally be preferred that the expressing cell used in the first round was not the cell line used for immunization and that the cell line used for immunization was used in the second (or subsequent) round of screening. This means that when phages are retained from the first round which bind to the expressing/transfected cell and are put into the second round with the expressing/transfected cell used for immunization the only main common antigen is the antigen of interest meaning that many of the unwanted antibodies, for example antibodies to other cell membrane proteins, are removed. This can hence give rise to more efficient screening.

As set out above, such initial rounds of screening, if used, can then be followed by subjecting the positive clones to further screening to assess whether or not they also do not have the ability to bind the first antigen, i.e. have the ability to discriminate between the membrane bound and soluble forms of the antigen.

The antibodies which will be identified after step (iv) of the method will be those which can discriminate between the membrane bound form of an antigen and the soluble form of the antigen. Other desired properties of the antibodies can also be readily selected for, e.g. antibodies can be selected which block the function of the antigen, e.g. block the binding of ligand to the membrane bound receptor, or which activate (or agonise) the function of the antigen, e.g. mimic the binding of ligand to the membrane bound receptor, or which simply recognise the antigen and do not inhibit or activate the function thereof. Other desired properties which could be selected for are antibodies which display antibody dependent cell mediated cytotoxicity (ADCC) or complement dependent cell (CDC) activity. Monoclonal antibodies are generally preferred.

The type of antibody identified at the end of step (iv) will necessarily be determined by the types of candidates which are screened. Thus, if hybridoma technology is used to obtain the candidate antibodies for screening then the antibodies which come out of the screening will be murine antibodies (or antibodies from whatever species is used to derive the B cells used in the hybridoma techniques). Alternatively, if antibody expression libraries are generated using recombinant techniques, then the antibodies which come out of the screening will take the particular format of the library chosen. Because of the way such recombinant libraries are generated such candidates will contain a random pairing of heavy and light antibody chains which will give rise to another element of diversity in the antibodies which are screened (see for example the exemplified phage display screening methods). Thus, by virtue of genetic engineering when the antibody expression libraries are formed, it can be seen that the antibodies which are generated by the methods of the invention are not limited to whole antibodies but can be antibody fragments that comprise an antigen binding domain such as Fab', Fab, F(ab')$_2$, single domain antibodies (DABs), TandAbs dimer, Fv, scFv (single chain Fv), dsFv, ds-scFv, Fd, linear antibodies, minibodies, diabodies, bispecific antibody fragments and the like. Indeed the generation of a phage display library of Fab fragments is exemplified herein.

Equally, it will be appreciated that such antibody fragments can be engineered from a particular antibody if required. Thus, if a discriminating antibody has been selected in accordance with the methods of the invention, then this antibody can be converted to any other desired format, for example to any desired type of antibody fragment such as those listed above, by appropriate methods. In addition, any such antibody or antibody fragment can be further conjugated to other useful agents to form an immunoconjugate. For example, in a preferred aspects, an immunoconjugate comprising an antibody of the invention is provided. Preferred immunoconjugates will carry a payload such as a radio-isotope, toxin or chemotherapeutic agent.

In preferred embodiments, the antibodies are non-human, e.g. murine antibodies or comprise murine antibody sequences (i.e. the sources of the VH and VL chains are murine), or are from another type of non-human animal such as those described elsewhere herein. In such cases, if desired, once selected these antibodies can be subjected to humanization protocols using methods which are standard and well known in the art. These antibodies can also readily be made into chimeric antibodies where a human Fc region is added to the non-human antibody, or a human Fc region is substituted for the non-human Fc region already present. Non-human Fab antibodies such as the mouse Fab antibodies identified by phage display techniques such as those described herein are particularly suited to the formation of chimeric antibodies. If it is desired to use the antibodies for therapeutic purposes then such steps are likely to be preferred, although it should also be noted that non-human antibodies can be used for therapy of humans providing that the HAMA (Human Anti-Mouse Antibody) response can be controlled. Indeed OKT3 is an example of such an antibody.

The methods of the invention have been shown to generate a large number of different isotypes of antibody (for example IgM, IgG1 and IgG2a, etc) showing the diversity of the antibodies which are produced.

The methods of the invention can thus be used to generate, select or identify an antibody which can discriminate between the membrane bound form of an antigen and the soluble form of the antigen, which can then be isolated, produced or manufactured for various downstream uses. As such, antibodies generated, identified or selected using the methods of the invention form a further aspect of the invention. Thus, a further aspect of the present invention provides a method of generating, selecting, identifying and/or isolating an antibody which can discriminate between the membrane bound form of an antigen and the soluble form of the antigen, said method comprising the steps (i) to (iv) as described herein to select an antibody which can discriminate between the membrane bound form of an antigen and the soluble form of the antigen, and optionally (e) identifying and/or isolating the relevant antibody molecule.

Once appropriate nucleic acid fragments encoding the antibodies have been identified, the nucleic acids encoding the antibodies can, if desired, be subjected to affinity maturation, for example to try and identify antibodies with further improved properties. Such affinity maturation can be performed by carrying out any conventional form of mutagenesis, including but not limited to the addition, deletion and/or substitution of one or more nucleotides in a controlled (e.g. site directed mutagenesis) or random manner, error-prone PCR, domain swapping, cassette mutagenesis and chain shuffling, etc.

When one or more antibodies have been generated, selected, identified, isolated and/or purified using the methods of the invention, these candidates, or a component, fragment, variant, or derivative thereof may be manufactured and if desired formulated with at least one pharmaceutically acceptable carrier or excipient. Such manufactured molecules, or components, fragments, variants, or derivatives thereof, are also encompassed by the present invention. Alternatively, these molecules may take the form of nucleic acids encoding said antibodies, which nucleic acids may in turn be incorporated into an appropriate expression vector and/or be contained in a suitable host cell. Thus, nucleic acid molecules encoding said antibodies, or expression vectors containing said nucleic acid molecules form further aspects of the invention.

Once a particular antibody, or a component, fragment, variant, or derivative thereof, has been selected, identified, etc., in accordance with the present invention, the expression vector encoding the antibody can readily be used (or adapted for use) to produce sufficient quantities of the molecule by expression in appropriate host cells or systems and isolating the antibodies from the host cell or system or from the growth medium or supernatant thereof, as appropriate.

Thus, a yet further aspect of the invention provides a method of producing or manufacturing an antibody comprising the steps of generating, identifying or selecting the antibody according to the methods of the invention as described above, manufacturing or producing said antibody, or a component, fragment, variant, or derivative thereof and optionally formulating said manufactured antibody with at least one pharmaceutically acceptable carrier or excipient.

Said variants or derivatives of an antibody include peptoid equivalents, molecules with a non-peptidic synthetic backbone and polypeptides related to or derived from the original identified polypeptide wherein the amino acid sequence has been modified by single or multiple amino acid substitutions, additions and/or deletions which may alternatively or additionally include the substitution with or addition of amino acids which have been chemically modified, e.g. by deglycosylation or glycosylation. Conveniently, such derivatives or variants may have at least 60, 70, 80, 90, 95 or 99% sequence identity to the original polypeptide from which they are derived.

As the invention relates to the generation of antibodies, said variants or derivatives further include the conversion of one format of antibody molecule into another format (e.g. conversion from Fab to scFv or vice versa, or the conversion between any format of antibody molecules described elsewhere herein, e.g. the conversion to any other type of antibody fragment as described herein), or the conversion of an antibody molecule to a particular class of antibody molecule (e.g. the conversion of an antibody molecule to IgG or a subclass thereof, e.g. IgG1 or IgG3, which are particularly suitable for therapeutic antibodies) or the humanization or the formation of a chimeric version of any antibody.

Said variants or derivatives further include the association of antibodies with further functional components which may for example be useful in the downstream applications of said antibodies. For example the antibodies may be associated with components which target them to a particular site in the body, or with detectable moieties useful for example in imaging or other diagnostic applications, or with a payload such as a radio-isotope, toxin or chemotherapeutic agent in the form of an immunoconjugate.

Clearly, the main requirement for such components, fragments, variants, or derivative binding partner molecules or target entities is that they retain their original functional activity in terms of binding ability or have improved functional activity.

The antibody molecules isolated, detected, selected, identified or manufactured using the methods of the present invention may be used in any methods where antibodies specific to a target entity (for example antibodies specific to a particular antigen) are required. Thus, the antibodies can be used as molecular tools and a further aspect of the invention provides a reagent which comprises such antibodies as defined herein. In addition, such molecules can be used for in vivo therapeutic or prophylactic applications, in vivo or in vitro diagnostic or imaging applications, or in vitro assays.

Thus, yet further aspects of the invention provide such generated, selected or manufactured antibody molecules for use in therapy or in vivo diagnosis or imaging or for use in any of the other applications mentioned above. Also provided is the use of such antibody molecules in the manufacture of a medicament or composition for use in therapy (in particular cancer therapy) or in vivo diagnosis or imaging or for use in any of the other applications mentioned above. Methods of treatment of a patient comprising the administration of an effective dose of such an antibody molecule are also provided. Preferred therapy is cancer therapy, (e.g. therapy of solid tumors) but the invention can also be used to treat inflammation reactions (e.g. due to the antigen being present on or associated with a sub-type of T cells) and all undesirable reactions or diseases where the antigen in question plays a role.

Yet further aspects are methods of diagnosis or imaging of a patient comprising the administration of an appropriate amount of an antibody molecule produced by the methods as defined herein to the patient and detecting the presence, location and/or amount of the antibody molecule in the patient.

The antibody molecules produced by said methods may equally be used in methods of diagnosis which are carried out in vitro, if appropriate, e.g. carried out on a tissue sample or some other kind of sample, e.g. blood, obtained or derived from a patient.

In an alternative aspect, the present invention provides an antibody which can discriminate between the membrane bound form of an antigen and the soluble form of the antigen for use in therapy. In particular, the present invention provides an antibody which can bind to the membrane bound form of an antigen but which does not bind to the soluble form of the same antigen for use in therapy, preferably cancer therapy, (e.g. therapy of solid tumors). In alternative aspects, the present invention provides an antibody which can bind to the soluble form of an antigen but which does not bind to the membrane bound form of the same antigen for use in therapy, preferably cancer therapy, (e.g. therapy of solid tumors).

Such antibodies can also be used for in vivo diagnosis or imaging, preferably of cancer, e.g. of solid tumors.

Also provided is the use of such antibodies in the manufacture of a medicament or composition for use in therapy (in particular cancer therapy) or for use in in vivo diagnosis or imaging or for use in any of the other applications mentioned above. Methods of treatment of a patient comprising the administration of an effective amount of such antibodies are also provided. Preferred therapy is cancer therapy, (e.g. therapy of solid tumors).

Yet further aspects are methods of diagnosis or imaging of a patient comprising the administration of an appropriate amount of such an antibody to the patient and detecting the presence, location and/or amount of the antibody molecule in the patient.

Such antibody molecules may equally be used in methods of diagnosis which are carried out in vitro, if appropriate, e.g. carried out on a tissue sample or some other kind of sample, e.g. blood, obtained or derived from a patient.

The invention and some preferred embodiments will now be described in more detail in the following non-limiting Examples with reference to the following drawings in which:

FIG. 1 shows the profile of competition between a positive control antibody (B-R6 antibody) and serum. Flow cytometry results are shown in which the green curve (G) shows the profile of B-R6 antibody staining on a positive cell line, JV1. The red curve (R) shows the staining profile with an isotype control. The boxed figure shows the percentage of labelling. The B-R6 antibody is used at two dilutions (1/10 and 1/20) in the presence of either PBS, straight serum, or serum at a dilution of 1/2 or 1/5.

FIG. 2 shows the profile of competition between supernatant from a candidate antibody (4B3) and serum. Flow cytometry results are shown in which the green curve (G) shows the profile of 4B3 antibody staining on a positive cell line, JV1. The red curve (R) shows the staining profile with an isotype control. The boxed figure shows the MFI ratio. The 4B3 supernatant is used at four concentrations (straight supernatant (sn), 1/10 sn, 1/20 sn and 1/50) in the presence of either PBS, straight serum, or serum at a dilution of 1/5 or 1/10.

FIG. 3 shows the profile of competition between supernatant from a candidate antibody (6H3) and serum. Flow cytometry results are shown in which the green curve (G) shows the profile of 6H3 antibody staining on a positive cell line, JV1. The red curve (R) shows the staining profile with an isotype control. The boxed figure shows the percentage of labelling. The 6H3 supernatant is used at four concentrations (straight supernatant (sn), 1/2 sn, 1/10 sn and 1/20) in the presence of either PBS, or serum at a dilution of 1/2, 1/5 or 1/10.

FIG. 4 shows the profile of competition between supernatant from a candidate antibody (18G2) and serum. Flow cytometry results are shown in which the green curve (G) shows the profile of 18G2 antibody staining on a positive cell line, JV1. The red curve (R) shows the staining profile with an isotype control. The boxed figure shows the percentage of labelling. The 18G2 supernatant is used at four concentrations (straight supernatant (sn), 1/10 sn, 1/20 sn and 1/50) in the presence of either PBS, straight serum, or serum at a dilution of 1/5 or 1/10.

Figure 7A:
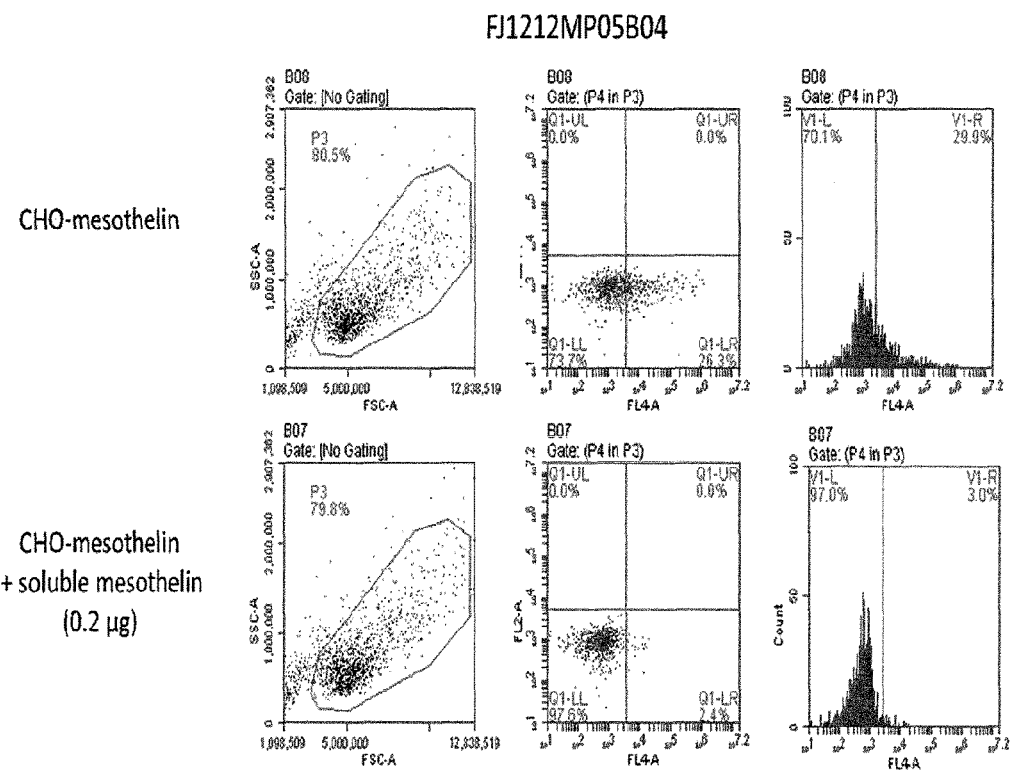
Figure 7B:
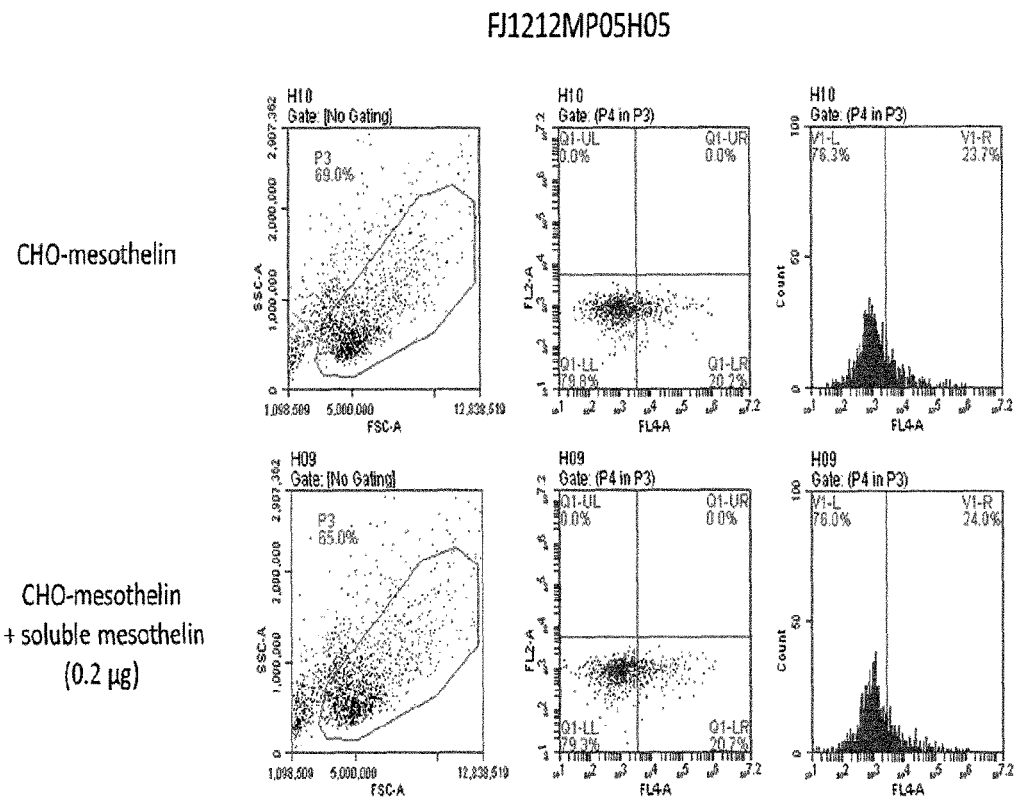

FIGS. 7A and 7B show flow cytometry analysis for periplasmic extracts (P.E.s) binding to mesothelin expressing CHO cells in the presence or the absence of soluble mesothelin at a concentration of 0.2 µg. For each sample, the cell population to be analyzed was first gated according to Forward Scatter (FSC) vs Side Scatter (SSC) parameters. P.E.s binding levels were then analyzed by looking at the percentage of positive dots in the Q1-LR quadrant (FL4-A channel detector). The values of the FL4-A Mean intensity were also noted.

EXAMPLES

Example 1: Generation of Antibodies which can Discriminate Between Membrane Bound gp80 and Soluble gp80

Table 1 shows the protocol of immunization used for the GP80 antigen.

A) Immunization:

TABLE 1

Protocol of immunization of 3 mice used for the fusion

| | Date | Tolerance | Injected Solution |
|---|---|---|---|
| J0 | 21 Jun. 2011 | IP 1 | 10 ug/mouse of soluble GP80 then 1 mg/mouse/200 µl of CP (10 min after IP with antigen) |
| J1 | 22 Jun. 2011 | | 1 mg/mouse/200 µl of CP |
| J2 | 23 Jun. 2011 | | 1 mg/mouse/200 µl of CP |
| J14 | 05 Jul. 2011 | IP 2 | 10 ug/mouse of soluble GP80 then 1 mg/mouse/200 µl of CP (10 min after IP with antigen) |

TABLE 1-continued

Protocol of immunization of 3 mice used for the fusion

|  | Date | Tolerance | Injected Solution |
|---|---|---|---|
| J15 | 06 Jul. 2011 |  | 1 mg/mouse/200 µl of CP |
| J16 | 07 Jul. 2011 |  | 1 mg/mouse/200 µl of CP |
| J28 | 19 Jul. 2011 | IP 3 | 10 ug/mouse of soluble GP80 then 1 mg/mouse/200 µl of CP (10 min after IP with antigen) |
| J29 | 20 Jul. 2011 |  | 1 mg/mouse/200 µl of CP |
| J30 | 21 Jul. 2011 |  | 1 mg/mouse/200 µl of CP |
| J42 | 02 Aug. 2011 | IP 4 | 10 ug/mouse of soluble GP80 then 1 mg/mouse/200 µl of CP (10 min after IP with antigen) |
| J43 | 03 Aug. 2011 |  | 1 mg/mouse/200 µl of CP |
| J44 | 04 Aug. 2011 |  | 1 mg/mouse/200 µl of CP |
|  |  | Immunization |  |
| J45 | 05 Aug. 2011 | IP1 | 10M JV1/mouse |
| J59 | 19 Aug. 2011 | IP2 | 10M JV1/mouse |
| J73 | 02 Sept. 2011 | IP3 | 10M JV1/mouse |
| J87 | 16 Sept. 2011 | IP4 | 10M JV1/mouse |
| J101 | 30 Sept. 2011 | Boost IV | 1M JV1/mouse in IV |

In the above immunization protocol, the soluble GP 80 is recombinant human soluble IL-6 receptor alpha (gp80) obtained from Seralab. CP or cyclophosphamide is Cyclophosphamide monohydrate obtained from Sigma. BalbC mice were used. For lymph nodes the antigen in PBS (1 µg or 1 million (M) cells) is injected in the foot pad. For spleens the antigen in PBS (10 µg or 10 million (M) cells) is injected IP.

B) Test Quality of the JV1 Cells Expression During the Immunization:

JV1 cells (Baf3 including the human membrane gp80) were assessed for gp80 expression during the immunization process to qualify the presence of the antigen. The Table 2 summarizes the results of obtained gp80 expression. Membrane staining of gp80 was performed on $2\times10^5$ cells with 1 µg antibody (BR-6 FITC, Diaclone). The Baf3 cells were obtained from Montpellier, France.

TABLE 2

Membrane staining of gp80 on the JV1 cells. Results were expressed as mean % of positive cells and as the ratio of mean fluorescence intensity (MFI).

| Date | % labelling | Ratio MFI |
|---|---|---|
| 18 Jul. 2011 | 72 | 2.60 |
| 18 Aug. 2011 | 89 | 2.30 |
| 02 Sept. 2011 | 68 | 2.20 |
| 21 Sept. 2011 | 62 | 1.70 |
| 17 Oct. 2011 | 53 | 2.20 |

C) Quality Control of Serums During the Immunization:
a) By Flow Cytometry (Control of the Specificity)

To control the effectiveness of mice immunization with JV1, serums were taken after the fourth immunization to assess the presence of anti-gp80 antibodies. For this purpose, serum were diluted several times and used to stain directly JV1 cells and a gp-80 negative cell line as a control. Then, cells were washed three times and exposed to an anti-mouse antibody (Cappel, M P). Cells were analysed by flow cytometry.

When such tests were carried out on serums taken from immunized mice on 21 Sep. 2011, significant amounts of anti-gp80 antibodies were shown to be present in the serums after the fourth immunization in comparison with the amounts of anti-gp80 antibodies present in healthy (non-immunized) mouse serums (data not shown). No significant staining was observed on the gp-80 negative cell line. This shows that the immunization protocol with membrane bound gp-80 is working.

b) By ELISA (Isotype Control of Serums)

Since the class switch commitment from IgM to IgG is an important feature of B cell memory induction, we assessed as a quality control, the distribution of Immunoglobulin subtypes following the immunization protocols. Our results showed that most immunoglobulins detected are IgG.

By an ELISA method, we determined the most present isotype in the serum. Knowing that the presence of IgM corresponds to a low immunization and that of the IgG1 and IgG2a corresponds to a good immunization. With the dilutions of 1/10 000 and 1/100 000, we determined that we have a majority of IgG1, i.e. a sign of a good immunization.

D) Fusion of 4 Oct. 2011:

Splenocytes were harvested from 3 mice and used to generate hybridoma fusions as follows (M=million):

TABLE 3

Summary of the fusion

| Mouse | Splenocyte numbers used | Number of splenocytes used for the fusion | Number of 96 well-plate | Number of X6.3 used |
|---|---|---|---|---|
| 1 | 132M | 66M | 7 | 13.2M |
| 2 | 126M | 63M | 6 | 12.6M |
| 3 | 164M | 82M | 8 | 16.4M |
|  |  |  | 21 plates |  |

Splenocytes not used for the fusions were frozen in 90% serum and 10% DMSO.

Addition of HAT 4× on 5 Oct. 2011 to kill the not fused myeloma (×6.3).

Addition of HAT 2× on 14 Oct. 2011, next removed 100 µl from every well, e.g. for screening.

E) Screening:

The screening was realised by flow cytometry with the JV1 cells (positive cells expressing the IL-6 receptor/gp80) and JV0 cells (negative cells not expressing the IL-6 receptor/gp80). We selected candidate monoclonal antibodies recognizing JV1 cells and unable to bind JV0 cells.

Of the 64 candidates identified during the first screening step, 33 displayed a stable expression of anti-gp80 during hybridoma culture. These 33 candidates were then selected for cloning and nine of these candidates were selected for characterization.

F) Characterisation of these Antibodies:
a) Phenotype of these Candidates

TABLE 4

Summary of phenotype of candidates on different cell lines.

| Candidates | JV1 | JV0 |
|---|---|---|
| 4B3 | + | − |
| 6H3 | + | − |
| 6H7 | + | − |
| 12H12 | + | − |
| 18G2 | + | − |
| 19A8 | + | − |
| 19E8 | + | − |
| 21C6 | + | − |
| 21D11 | + | − |
| Ctrl +: B-R6 | + | − |

B-R6 antibody (Diaclone) is a monoclonal antibody specific for GP80 and is used as a positive control.

b) Isotype of these Candidates:

To know the serological class of antibodies (isotype) produced by the hybridomas, we made an ELISA.

For this purpose, supernanant of antibody is diluted at the 1/100 dilution before being to captured by a pre-coated polyclonal goat-anti mouse. After three washes, we added the detection antibody (specific of each isotype). After 60 minutes and three washes, TMB substrate is added to reveal the antibody isotype based on which wells produce color.

TABLE 5

Summary of isotype determination by ELISA method

| Candidates | Isotype |
|---|---|
| 4B3 | IgM |
| 6H3 | IgG1 |
| 6H7 | IgG1 |
| 12H12 | IgM |
| 18G2 | IgG1 |
| 19A8 | IgG2a |
| 19E8 | IgG1 |
| 21C6 | IgM |
| 21D11 | IgM | c) Specific Targeting of Membrane-Associated GP80 (IL-6R):

We made a competition test with antibodies to test the interaction of selected antibodies with the soluble form of GP80 (soluble protein or healthy human serum containing soluble gp80/IL-6R) and the membrane shape (present on cells).

By flow cytometry it was tested if the selected antibodies recognize the membrane GP80 in the presence of the soluble GP80.

Figure 1:
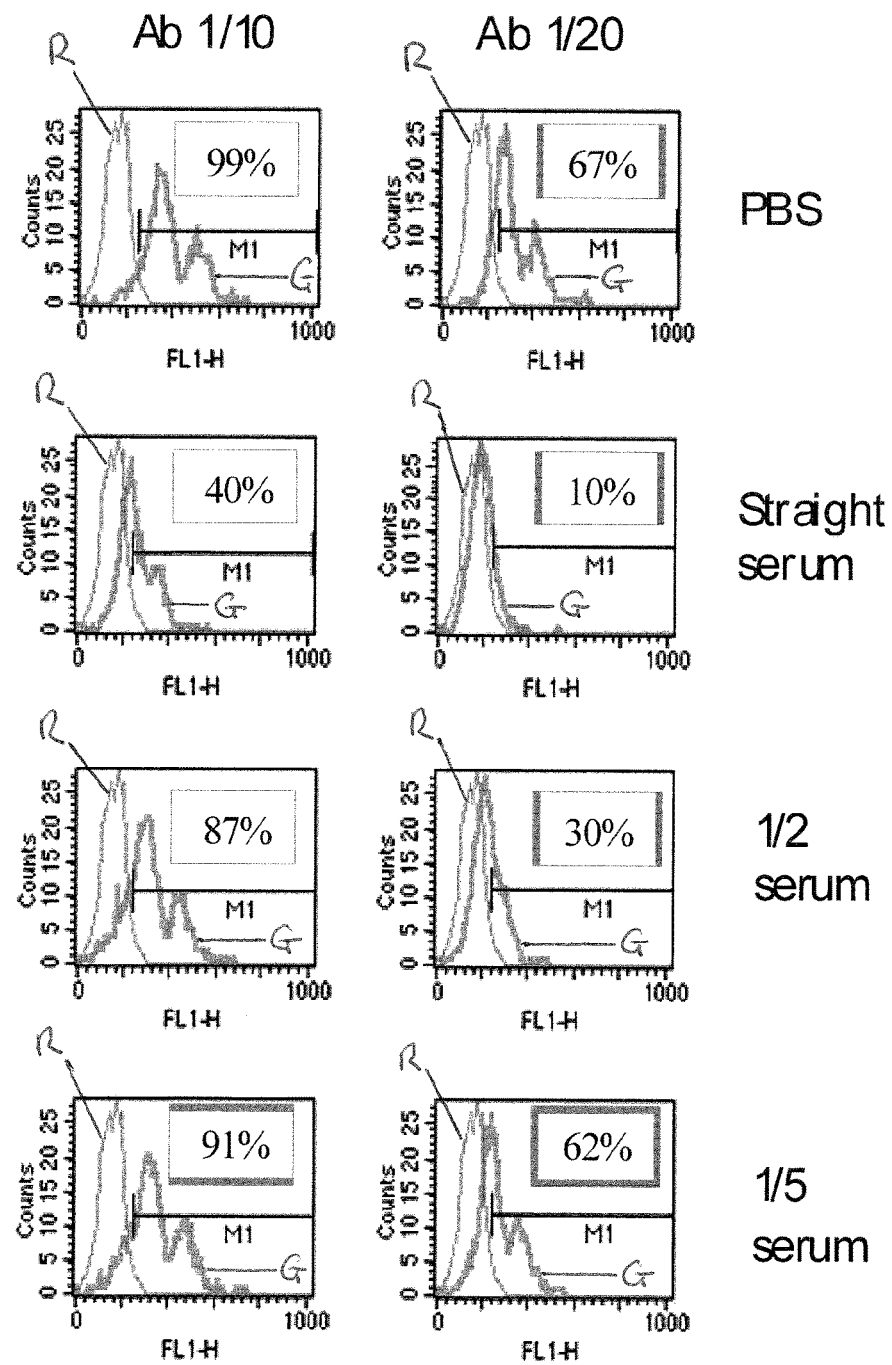

As a control, competition assays with an Ab recognizing the soluble and membrane bound GP80 (B-R6 Diaclone) were performed using healthy human serum (FIG. 1).

In FIG. 1, the green curve (marked G) shows the profile of antibody on a positive cell line, JV1. The red curve (marked R) shows the profile with an isotype control. The boxed figure shows the percentage of labelling. It can be noted that the green curve, G (Ab in competition) gets closer to the red one, R (negative) with pure serum (i.e. the highest concentration of soluble GP80).

The decrease of membrane GP80 staining is inversely correlated to the serum dilution. In other words, the more the serum is diluted (i.e. the lower the concentration of soluble GP80), the more the green curve gets closer to the normal profile like B-R6 without competition (PBS).

These results show that the Ab B-R6 made competition with serum, thus confirming that this antibody can bind to both soluble GP80 and membrane bound GP80.

Figure 2:

In FIG. 2, results of a similar competition assay are presented using hybridoma supernatant from the candidate antibody 4B3 instead of B-R6. The figure in the boxes shows the MFI ratio, e.g. 445.

The results in FIG. 2 show that the serum (containing soluble GP80) shows very little if any competition with the candidate clone 4B3. Thus, the candidate 4B3 is specific to the membrane form of GP80 and is not inhibited by soluble GP80. This antibody is thus an example of an antibody of the invention that binds to the membrane bound form of an antigen (GP80) but which does not bind to the soluble form of the antigen (GP80).

Figure 3:
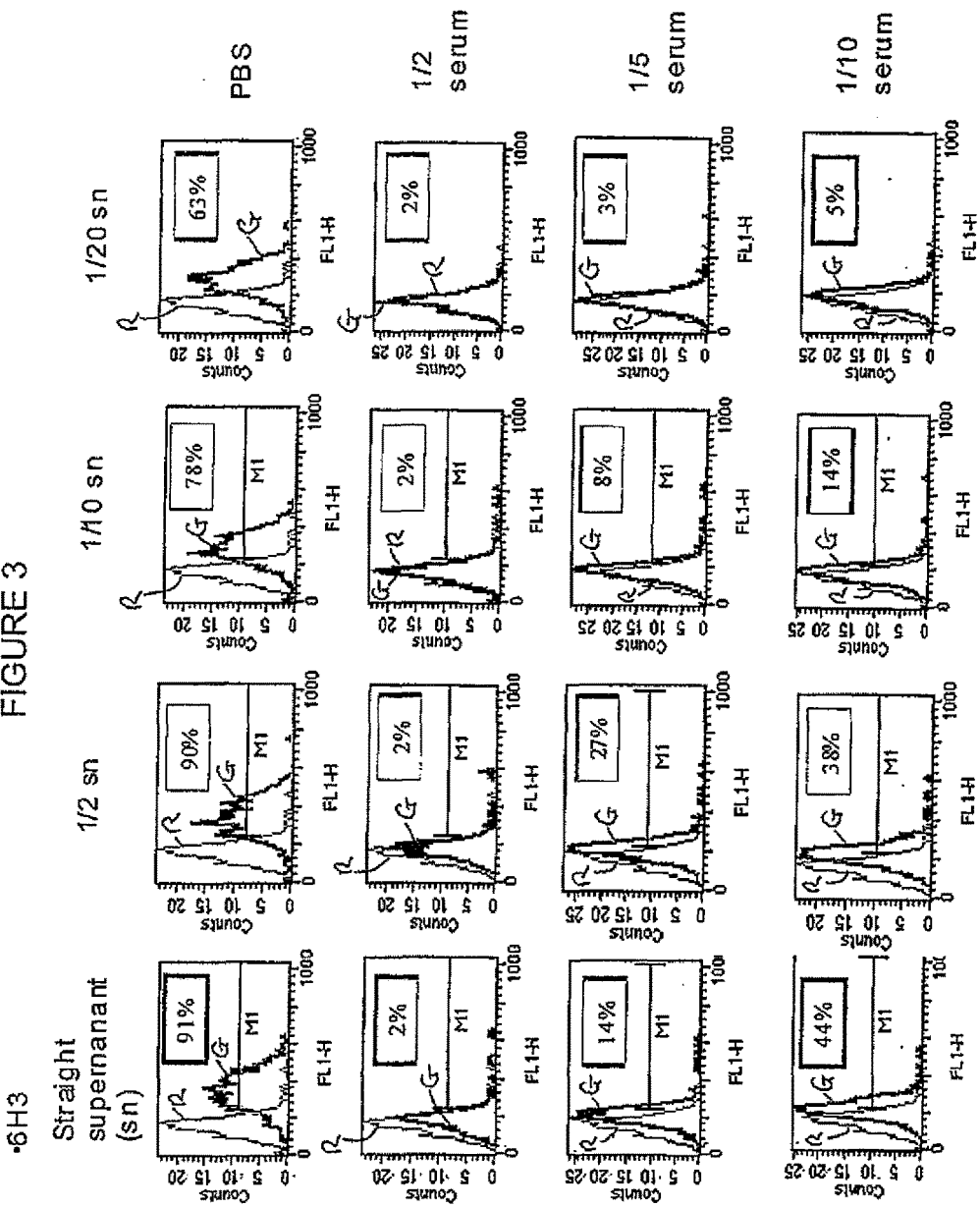

The competition assay was then carried out with hybridoma supernatant from candidate 6H3 (see FIG. 3).

The results in FIG. 3 show that the serum (containing soluble GP80) does compete with the candidate clone 6H3 for binding to JV1 cells. Thus, the candidate antibody 6H3 recognises both the membrane and the soluble form of GP80, i.e. is not an antibody of the invention as it does not discriminate.

Figure 4:
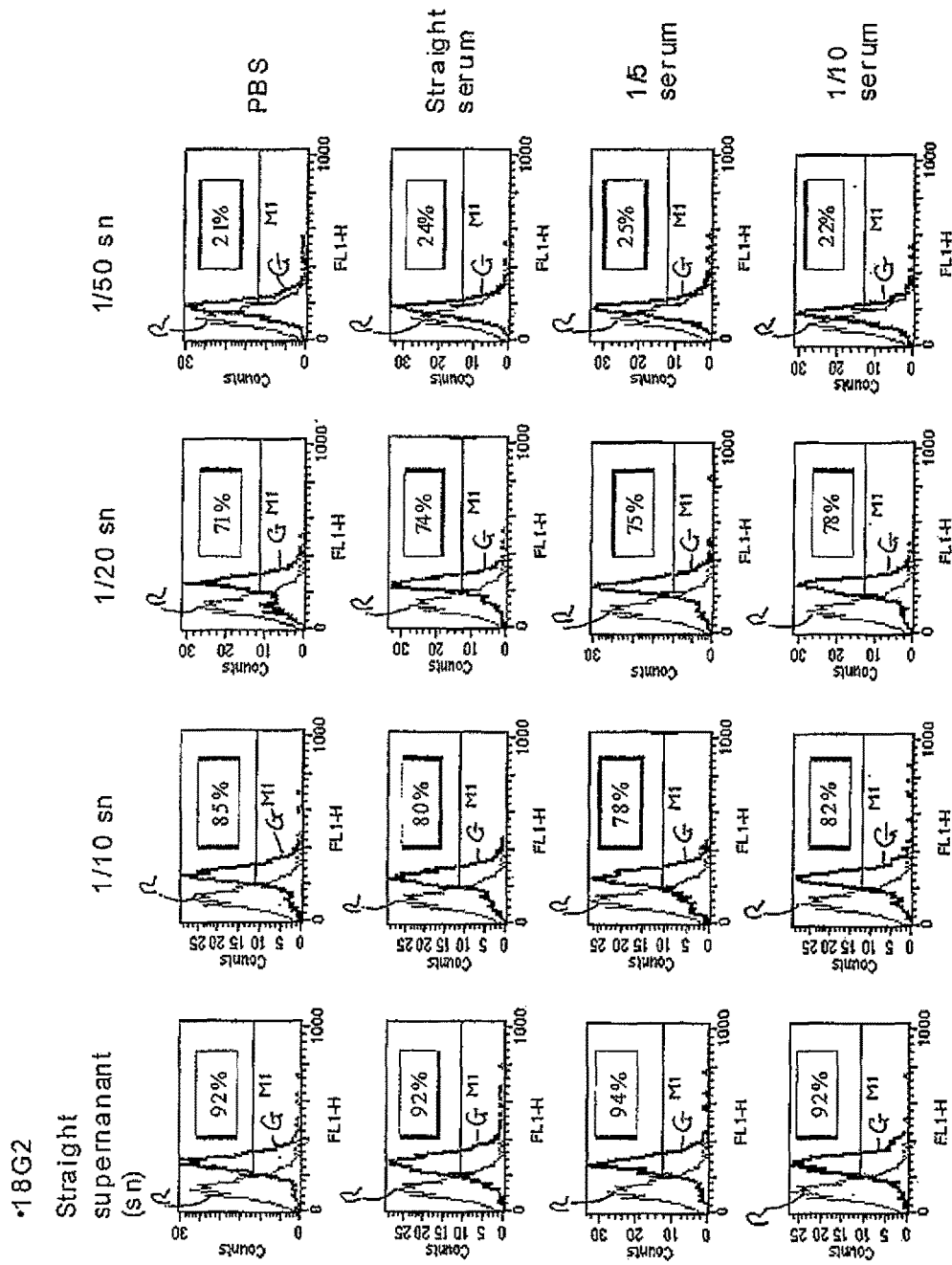

The competition assay was then carried out with hybridoma supernatant from candidate 18G2 (see FIG. 4).

The results in FIG. 4 show that the serum (containing soluble GP80) shows very little if any competition with the candidate clone 18G2. Thus, the candidate 18G2 is specific to the membrane from of GP80 and is not inhibited by soluble GP80. This antibody is thus an example of an antibody of the invention that binds to the membrane bound form of an antigen (GP80) but which does not bind to the soluble form of the antigen (GP80).

The competition assay was repeated with each of the remaining candidates, i.e. 21D11, 21C6, 12H12, 19E8, 19A8 and 6H7 and none of these showed any significant competition with the serum, i.e. the results (data not shown) were similar to those of 18G2 and 4B3. These antibodies are thus yet further examples of discriminating antibodies of the invention.

Thus, of the 9 candidates which were generated using the methods of the invention and were characterised further, it can be seen that 8 of these 9 showed the desired discriminating property, i.e. the ability to bind to the membrane bound form of an antigen (GP80) but not to bind to the soluble form of the antigen (GP80). This shows how powerful and reliable the method of the invention is in the generation of such discriminating antibodies.

Example 2: Generation of Antibodies which can Discriminate Between Membrane Bound Mesothelin and Soluble Mesothelin This example demonstrates the generation of antibodies that bind to the membrane bound mesothelin receptor, but not the soluble mesothelin receptor, from mice subjected to a tolerance immunization protocol in which in a first stage mesothelin soluble protein induced B-cells are depleted in vivo and in which in a second stage mice are boosted with P815 cells expressing mesothelin.

Immunization Protocol

Table 6 shows the protocol of immunization used for the mesothelin antigen.

TABLE 6

Protocol of immunization of 5 mice

| Date | Tolerance | | Injected Solution |
|---|---|---|---|
| J0 | 27 Feb. 2013 | IP 1 | 10 ug/mouse of soluble mesothelin then 1 mg/mouse/200 µl of CP (10 min after IP with antigen) |
| J1 | 28 Feb. 2013 | | 1 mg/mouse/200 µl of CP |
| J2 | 01 Mar. 2013 | | 1mg/mouse/200 µl of CP |
| J14 | 13 Mar. 2013 | IP 2 | 10 ug/mouse of soluble mesothelin then 1 mg/mouse/200 µl of CP (10 min after IP with antigen) |
| J15 | 14 Mar. 2013 | | 1 mg/mouse/200 µl of CP |
| J16 | 15 Mar. 2013 | | 1 mg/mouse/200 µl of CP |
| J28 | 27 Mar. 2013 | IP 3 | 10 ug/mouse of soluble mesothelin then 1 mg/mouse/200 µl of CP (10 min after IP with antigen) |
| J29 | 28 Mar. 2013 | | 1 mg/mouse/200 µl of CP |
| J30 | 29 Mar. 2013 | | 1 mg/mouse/200 µl of CP |

TABLE 6-continued

Protocol of immunization of 5 mice

| Date | Tolerance | | Injected Solution |
|---|---|---|---|
| J42 | 09 Apr. 2013 | IP 4 | 10 ug/mouse of soluble mesothelin then 1 mg/mouse/200 µl of CP (10 min after IP with antigen) |
| J43 | 10 Apr. 2013 | | 1 mg/mouse/200 µl of CP |
| J44 | 11 Apr. 2013 | | 1 mg/mouse/200 µl of CP |
| | | Immunization | |
| J45 | 12 Apr. 2013 | IP1 | 10M P815 mesothelin expressing cells/mouse IP |
| J59 | 26 Apr. 2013 | IP2 | 10M P815 mesothelin expressing cells/mouse IP |
| J73 | 10 May 2013 | IP3 | 10M P815 mesothelin expressing cells/mouse IP |
| J87 | 24 May 2013 | IV Boost | 1M cells/mouse IV |
| J91 | 28 May 2013 | Fusion | |

In the above immunization protocol, the soluble mesothelin was recombinant human mesothelin (sourced from RayBiotech Inc., Catalog No. 230-00043). The P815 wild type cells were obtained from ATCC and transfected with a vector construct encoding human mesothelin (sc304006 from ORIGENE, vector pCMV6-XL4) to generate the P815-mesothelin expressing cells. CP or cyclophosphamide is cyclophosphamide monohydrate obtained from Sigma. BalbC mice were used. For lymph nodes the antigen in PBS (1 µg or 1 million (M) cells) is injected in the foot pad. For spleens the antigen in PBS (10 µg or 10 million (M) cells) is injected IP. The other details of immunization are as described above in Example 1. A total of five mice were immunized with P815-mesothelin expressing cells after tolerance induction against soluble mesothelin.

The 5 mice were sacrificed, the spleens taken out and spleen cells put into suspension. 25 million splenocytes from each spleen were combined after which hybridoma fusions were generated with x6.3 as described in Example 1, and 12 plates were prepared for screening.

Screening of Hybridomas

The screening of 64 hybridomas was carried out by flow cytometry as described in Example 1 with the P815-mesothelin cells (positive cells expressing the mesothelin receptor) and P815-wild type cells sourced from ATCC (negative cells not expressing the mesothelin receptor). 2 candidate monoclonal antibodies were selected recognizing P815-mesothelin cells and unable to bind P815-wild type cells.

From these candidates further screening was carried out by FACS competition assay as described in Example 1 using P815-mesothelin cells and soluble mesothelin at concentrations of 0.5 µg and 1 µg in order to identify antibodies which recognized the membrane bound form of mesothelin but not the soluble form. The anti-mesothelin antibody (from R&D Systems FAB32652F) which binds to both membrane bound and soluble mesothelin was used as a control. Both clones showed the desired discriminating property, i.e. the ability to bind to the membrane bound form of mesothelin but not to bind to the soluble form of mesothelin (data not shown). These experiments, which resulted in the generation of discriminatory antibodies using a different antigen, further confirms the reliability of the method of the invention in the generation of such discriminating antibodies.

Isolation of Fabs Against Mesothelin by Constructing Phage Display Libraries

Figure 5:
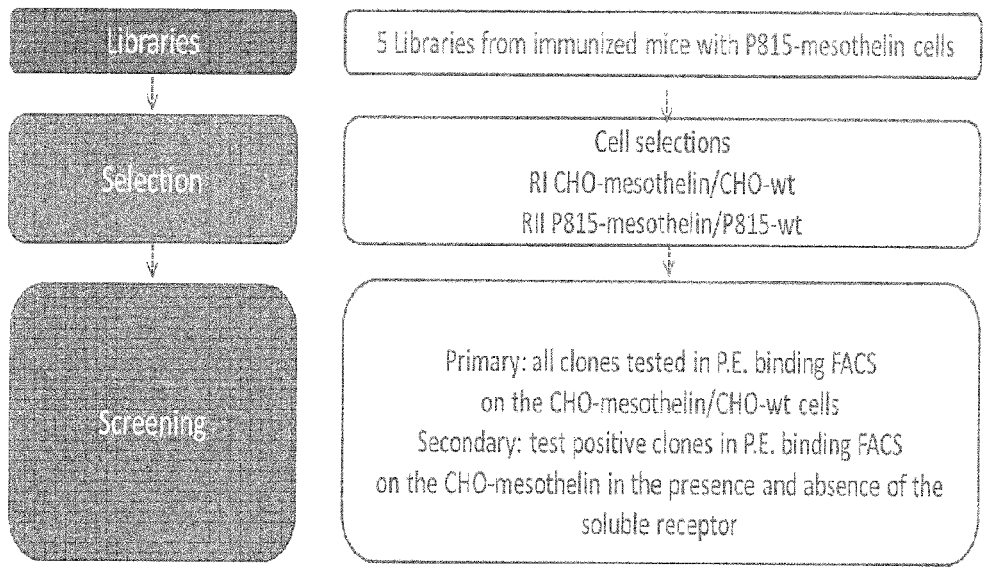
FIG. 5 shows an overview of the process used to select specific anti-membrane bound mesothelin Fabs.

An overview of the process followed to isolate anti membrane bound mesothelin specific Fabs is shown in FIG. 5. Mouse Fab libraries were used to select anti membrane bound mesothelin specific Fabs by phage display. In total, 5 libraries were selected on 2 rounds of cell selections against the CHO-Mesothelin and P815-Mesothelin. The resulting Fabs were screened for binding and specificity for membrane expressed mesothelin vs soluble mesothelin via FACS.

Library Construction

From the RNA extracted from the spleens of the mesothelin immunized mice (using the Qiagen RNeasy Maxi Kit (ref: 75162), cDNA was generated by RT-PCR (using Kit SuperScript™ First Strand Synthesis System, Invitrogen ref: 18080-051 and Kit Phusion Ozyme ref: F-530L). Per animal two sub-libraries were constructed (heavy-chain and light kappa-chain), using PCR with appropriate primers, the first primers of which are non-tagged primers and the second primers of which are tagged for insertion into the phagemid vector PCB3 (base vector pCES1). All sub-libraries passed the quality control of size above $5 \times 10^7$ and insert percentage above 80%.

The Fab phage display libraries were then constructed by combining the VHCH and the VκCκ genes from each animal. The five Fab libraries passed the quality control of size above $1 \times 10^8$ and insert percentage above 80%.

Selection of Anti Membrane Bound Mesothelin Fabs

Figure 6:
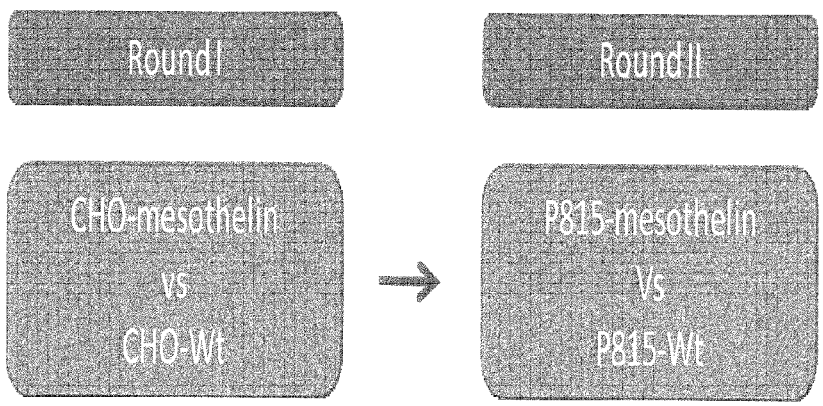
FIG. 6 shows an overview of the two rounds of selection conditions used to screen the Fab phage display libraries.

Phage libraries are generated for screening by standard protocols using VCSM13 helper phage and E. coli TG1 bacteria cells. The five phage libraries were each used in two consecutive rounds of cell selection as described in FIG. 6.

The cells used for selection were tested for mesothelin expression via FACS in parallel with the selection and passed the quality control as the Mean Channel Fluorescence values obtained with a FITC conjugated anti-human mesothelin antibody (R&D Systems FAB32652F) in the mesothelin expressing cells are 2-20 fold higher than in the wild type cells (data not shown).

In the first selection round the phage were incubated with CHO-mesothelin or CHO-wt cells (ATCC) in solution. The phage selected on mesothelin expressing cells were rescued and taken to a second round of selection. In the second selection round the phage were incubated with P815-mesothelin or P815-wt cells as described for the first round. All outputs from cells expressing mesothelin were rescued. TG1 glycerol stocks were prepared and stored at −70° C. The phage outputs were also used to infect logarithmically grown E. coli TG1 cells that were plated on agar plates (LBAGluc2% Amp100 µg/ml) for analysis.

Per output, one master plate (i.e. one plate for each phage library screened on CHO-mesothelin cells in Round I and P815-mesothelin cells in Round II) containing 96 monoclonal bacteria infected with selected phage was generated. The plates were stored in 20% glycerol at −70° C. and used for periplasmic extract (P.E.) production.

Screening of Specific Anti Membrane Bound Mesothelin Fabs

In order to determine the target specificity, the monoclonal Fabs produced from the clones picked after round II selection outputs were screened as periplasmic extracts (P.E.) in binding FACS on CHO-Mesothelin and CHO-WT cells.

In a primary screen, P.E. (diluted 1/5) from clones were tested for binding to Mesothelin expressing CHO cells on FACS using an anti-c-myc antibody together with a Goat Anti-Mouse Ig conjugated to APC fluorescent dye, as staining reagents. Fab binding levels were then analyzed by looking at the percentage of positive signal cells obtained using the FL4-A channel detector (as shown in the exemplary raw FACS data in FIG. 7A and FIG. 7B) and to the mean intensity levels of FL4 expression. Each monoclonal P.E. sample was also tested on non-expressing cells (CHO-wt) as a control.

The positive clones (i.e. the mesothelin binders) from the primary screening were tested in a similar experiment in the presence (0.2 and 1.36 μg) and absence of soluble mesothelin receptor. The results from this experiment are shown in Table 7 and the raw FACS data obtained from two exemplary clones can be seen in FIG. 7 (the clone shown in FIG. 7A being an example of a Fab clone which recognizes both the membrane bound form and the soluble form of mesothelin and the clone shown in FIG. 7B being an example of a Fab clone which is specific for the membrane bound form of mesothelin).

A summary of the frequencies of mesothelin binders from each library and their specificities is presented in Table 8.

TABLE 7

FACS analysis of P.E. of clones from the five Fab libraries selected on CHO-Mesothelin in the presence or absence of different amounts of soluble mesothelin.

| clone ID | CHO-mesothelin (%) | CHO-mesothelin + soluble mesothelin 0.2 μg (%) | fold reduction | CHO-mesothelin (%) | CHO-mesothelin + soluble mesothelin 1.36 μg (%) | fold reduction |
|---|---|---|---|---|---|---|
| MP01B01 | 3.5* | 2.7* | 1.3* | N.A. | N.A. | — |
| MP01D02 | 20.3** | 8.9** | 2.3** | 32** | 4.1** | 7.8** |
| MP01H03 | 15* | 6* | 2.5* | 29.5* | 33* | 0.9* |
| MP01A04 | 20.2* | 21.6* | 0.9* | 29.8* | 32* | 0.9* |
| MP01G04 | 8.1* | 6* | 1.4* | N.A. | N.A. | — |
| MP01B05 | 7.7* | 6* | 1.3* | N.A. | N.A. | — |
| MP01B08 | 5.4* | 6.6* | 0.8* | N.A. | N.A. | — |
| MP01D08 | 14.2* | 21.3* | 0.7* | 29.9* | 31.2* | 1.0* |
| MP01B06 | 7.3* | 9.9* | 0.7* | N.A. | N.A. | — |
| MP01H08 | 6.2* | 9.2* | 0.7* | N.A. | N.A. | — |
| MP01H07 | 17* | 24.6* | 0.7* | N.A. | N.A. | — |
| MP01C09 | 8.2* | 6.3* | 1.3* | N.A. | N.A. | — |
| MP01F09 | 15* | 9* | 1.7* | N.A. | N.A. | — |
| MP01C12 | 7.2* | 3.3* | 2.2* | N.A. | N.A. | — |
| MP02A01 | 13.6* | 20* | 0.7* | 28.4* | 29.6* | 1.0* |
| MP02C01 | 1.6* | 1.6* | 1.0* | N.A. | N.A. | — |
| MP02E01 | 14* | 25.8* | 0.5* | 27* | 27.6* | 1.0* |
| MP02F01 | 14* | 19.5* | 0.7* | N.A. | N.A. | — |
| MP02H01 | 13.5* | 24* | 0.6* | N.A. | N.A. | — |
| MP02A02 | 11.7* | 19.4* | 0.6* | N.A. | N.A. | — |
| MP02B02 | 13.4* | 20* | 0.7* | N.A. | N.A. | — |
| MP02C02 | 11.4* | 19.3* | 0.6* | N.A. | N.A. | — |
| MP02D02 | 11.6* | 19.3* | 0.6* | N.A. | N.A. | — |
| MP02E02 | 5.3* | 7.5* | 0.7* | 15.5* | 16.4* | 0.9* |
| MP02H02 | 15.9* | 14.60* | 1.1* | N.A. | N.A. | — |
| MP02A03 | 17.1* | 13.30* | 1.3* | N.A. | N.A. | — |
| MP02B03 | 14.9* | 12.60* | 1.2* | N.A. | N.A. | — |
| MP02C03 | 13.4* | 13.20* | 1.0* | N.A. | N.A. | — |
| MP02E03 | 14* | 13.10* | 1.1* | N.A. | N.A. | — |
| MP02G03 | 13.1* | 13.10* | 1.0* | N.A. | N.A. | — |
| MP02A04 | 14.8* | 11.90* | 1.2* | N.A. | N.A. | — |
| MP02B04 | 13.5* | 12.20* | 1.1* | N.A. | N.A. | — |
| MP02C04 | 10.8* | 12.70* | 0.9* | N.A. | N.A. | — |
| MP02D04 | 13.5* | 13.00* | 1.0* | N.A. | N.A. | — |
| MP02E04 | 12.1* | 12.20* | 1.0* | N.A. | N.A. | — |
| MP02F04 | 11.2* | 11.50* | 1.0* | N.A. | N.A. | — |
| MP02H04 | 12.9* | 11.00* | 1.2* | N.A. | N.A. | — |
| MP02B05 | 12.8* | 11.10* | 1.2* | N.A. | N.A. | — |
| MP02D05 | 12.2* | 10.80* | 1.1* | N.A. | N.A. | — |
| MP02E05 | 4.5* | 3.00* | 1.5* | N.A. | N.A. | — |
| MP02F05 | 11.4* | 9.60* | 1.2* | N.A. | N.A. | — |
| MP02A06 | 14* | 9.90* | 1.4* | N.A. | N.A. | — |
| MP02B06 | 12.1* | 10.10* | 1.2* | N.A. | N.A. | — |
| MP02C06 | 8.7* | 10.40* | 0.8* | N.A. | N.A. | — |
| MP02F06 | 11.4* | 9.50* | 1.2* | N.A. | N.A. | — |
| MP02G06 | 9.5* | 10.30* | 0.9* | N.A. | N.A. | — |
| MP02D08 | 7* | 5.80* | 1.2* | N.A. | N.A. | — |
| MP02F08 | 3.1** | 0.38* | 8.2* | N.A. | N.A. | — |
| MP02A07 | 10* | 10.43* | 1.0* | N.A. | N.A. | — |
| MP02B07 | 10.9* | 10.36* | 1.1* | N.A. | N.A. | — |
| MP02C07 | 8.7* | 10.29* | 0.8* | N.A. | N.A. | — |
| MP02F07 | 11.5* | 9.80* | 1.2* | N.A. | N.A. | — |
| MP02G07 | 3.9** | 1.58** | 2.5* | N.A. | N.A. | — |
| MP02A08 | 11.1* | 9.36* | 1.2* | N.A. | N.A. | — |
| MP02B08 | 3.6* | 1.36** | 2.6** | N.A. | N.A. | — |
| MP02C08 | 9* | 10.08* | 0.9* | N.A. | N.A. | — |
| MP02A09 | 10.7* | 9.90* | 1.1* | N.A. | N.A. | — |
| MP02C09 | 7.8* | 10.00* | 0.8* | N.A. | N.A. | — |
| MP02D09 | 0.9* | 9.40* | 0.1* | N.A. | N.A. | — |
| MP02E09 | 10.3* | 9.00* | 1.1* | N.A. | N.A. | — |

TABLE 7-continued

FACS analysis of P.E. of clones from the five Fab libraries selected on CHO-Mesothelin in the presence or absence of different amounts of soluble mesothelin.

| clone ID | CHO-mesothelin (%) | CHO-mesothelin + soluble mesothelin 0.2 μg (%) | fold reduction | CHO-mesothelin (%) | CHO-mesothelin + soluble mesothelin 1.36 μg (%) | fold reduction |
|---|---|---|---|---|---|---|
| MP02G09 | 9* | 9.10* | 1.0* | N,A. | N,A. | — |
| MP02H09 | 10.1* | 10.60* | 1.0* | N,A. | N,A. | — |
| MP02B10 | 10.2* | 10.00* | 1.0* | N,A. | N,A. | — |
| MP02C10 | 9* | 9.40* | 1.0* | N,A. | N,A. | — |
| MP02D10 | 10* | 9.60* | 1.0* | N,A. | N,A. | — |
| MP02E10 | 10.2* | 8.60* | 1.2* | N,A. | N,A. | — |
| MP02F10 | 9.3* | 9.80* | 0.9* | N,A. | N,A. | — |
| MP02G10 | 9.8* | 9.80* | 1.0* | N,A. | N,A. | — |
| MP02H10 | 4.4* | 3.00* | 1.5* | N,A. | N,A. | — |
| MP02B11 | 8.7* | 9.10* | 1.0* | N,A. | N,A. | — |
| MP02D11 | 10.2* | 8.10* | 1.3* | N,A. | N,A. | — |
| MP02E11 | 9* | 9.10* | 1.0* | N,A. | N,A. | — |
| MP02F11 | 10.4* | 8.70* | 1.2* | N,A. | N,A. | — |
| MP02H11 | 9.7* | 9.10* | 1.1* | N,A. | N,A. | — |
| MP02B12 | 9.7* | 7.30* | 1.3* | N,A. | N,A. | — |
| MP02C12 | 8.3* | 8.70* | 1.0* | N,A. | N,A. | — |
| MP02D12 | 10.8* | 9.10* | 1.2* | N,A. | N,A. | — |
| MP02E12 | 11.5* | 7.90* | 1.5* | N,A. | N,A. | — |
| MP02F12 | 10.4* | 8.30* | 1.3* | N,A. | N,A. | — |
| MP02G12 | 9.7* | 8.50* | 1.1* | N,A. | N,A. | — |
| MP03A01 | 11.1* | 9.5* | 1.2* | N,A. | N,A. | — |
| MP03B01 | 18.5* | 19* | 1.0* | 30.4* | 32.8* | 0.9* |
| MP03C01 | 21.4** | 6.2** | 3.5** | 30.1** | 3.2** | 9.4** |
| MP03E01 | 19.3** | 9.8** | 2.0** | N,A. | N,A. | — |
| MP03G01 | 20.7** | 0.9** | 23.0** | 22.7** | 1.4** | 16.2** |
| MP03B02 | 14.4** | 9** | 1.6** | N,A. | N,A. | — |
| MP03C02 | 23.3* | 20.4* | 1.1* | 32.6* | 33.7* | 1.0* |
| MP03F02 | 13.3* | 9.9* | 1.3* | N,A. | N,A. | — |
| MP03G02 | 17.5* | 7.1* | 2.5* | 17.6* | 21* | 0.8* |
| MP03A03 | 15.7* | 11.9* | 1.3* | N,A. | N,A. | — |
| MP03B03 | 14.4** | 8.5** | 1.7** | N,A. | N,A. | — |
| MP03C03 | 8.6* | 7.6* | 1.1* | N,A. | N,A. | — |
| MP03F03 | 11.3* | 10.4* | 1.1* | 18* | 18.7* | 1.0* |
| MP03H03 | 22.6* | 17.2* | 1.3* | 26.5* | 25.8* | 1.0* |
| MP03A04 | 13.7** | 8.8** | 1.6** | N,A. | N,A. | — |
| MP03C04 | 13.5* | 10.8* | 1.3* | N,A. | N,A. | — |
| MP03D04 | 14.5* | 8.50* | 1.7* | N,A. | N,A. | — |
| MP03F04 | 14.6* | 8.80* | 1.7* | N,A. | N,A. | — |
| MP03G04 | 11.5* | 7.90* | 1.5* | N,A. | N,A. | — |
| MP03B05 | 15.6* | 11.00* | 1.4* | N,A. | N,A. | — |
| MP03E06 | 8.3** | 2.80** | 3.0** | N,A. | N,A. | — |
| MP03G06 | 10.4* | 7.30* | 1.4* | N,A. | N,A. | — |
| MP03E07 | 7.9* | 5.30* | 1.5* | N,A. | N,A. | — |
| MP03B08 | 12.9* | 11.10* | 1.2* | N,A. | N,A. | — |
| MP03D08 | 8.4* | 8.20* | 1.0* | N,A. | N,A. | — |
| MP03E08 | 12** | 1.40** | 8.6* | N,A. | N,A. | — |
| MP03G08 | 15.6* | 15.70* | 1.0* | N,A. | N,A. | — |
| MP03H08 | 10.7* | 9.40* | 1.1* | N,A. | N,A. | — |
| MP03A09 | 14.7** | 2.40** | 6.1** | N,A. | N,A. | — |
| MP03C09 | 10.2* | 12.50* | 0.8* | N,A. | N,A. | — |
| MP03D09 | 11.6* | 9.00* | 1.3* | N,A. | N,A. | — |
| MP03H09 | 18.3* | 12.80* | 14* | N,A. | N,A. | — |
| MP03E10 | 12.5* | 10.10* | 1.2* | N,A. | N,A. | — |
| MP03G10 | 8.1* | 7.60* | 1.1* | N,A. | N,A. | — |
| MP03B11 | 8.6* | 8.40* | 1.0* | N,A. | N,A. | — |
| MP03C11 | 9.2* | 5.90* | 1.6* | N,A. | N,A. | — |
| MP03E11 | 10.2* | 8.00* | 1.3* | N,A. | N,A. | — |
| MP03F11 | 10.4* | 9.60* | 1.1* | N,A. | N,A. | — |
| MP03C12 | 5.1** | 1.50** | 3.4** | N,A. | N,A. | — |
| MP03F12 | 14.7** | 2.00** | 7.4** | N,A. | N,A. | — |
| MP04B01 | 2.8* | 2.8* | 1.0* | N,A. | N,A. | — |
| MP04G01 | 8* | 8.6* | 0.9* | N,A. | N,A. | — |
| MP04F04 | 8.4* | 8* | 1.1* | N,A. | N,A. | — |
| MP04C05 | 6.3* | 6* | 1.1* | N,A. | N,A. | — |
| MP04H05 | 4.9* | 5.9* | 0.8* | N,A. | N,A. | — |
| MP04E09 | 4* | 4.1* | 1.0* | N,A. | N,A. | — |
| MP04D10 | 7.8* | 5.6* | 1.4* | N,A. | N,A. | — |
| MP04E12 | 2.7* | 4.1* | 0.7* | N,A. | N,A. | — |
| MP04F12 | 3* | 3.1* | 1.0* | N,A. | N,A. | — |
| MP05D01 | 16.3* | 12.1* | 1.3* | N,A. | N,A. | — |
| MP05F01 | 8.4* | 7.5* | 1.1* | N,A. | N,A. | — |

TABLE 7-continued

FACS analysis of P.E. of clones from the five Fab libraries selected on CHO-Mesothelin in the presence or absence of different amounts of soluble mesothelin.

| clone ID | CHO-mesothelin (%) | CHO-mesothelin + soluble mesothelin 0.2 µg (%) | fold reduction | CHO-mesothelin (%) | CHO-mesothelin + soluble mesothelin 1.36 µg (%) | fold reduction |
|---|---|---|---|---|---|---|
| MP05D02 | 11.8** | 4** | 3.0** | N,A. | N,A. | — |
| MP05F03 | 14.3* | 11.7* | 1.2* | N,A. | N,A. | — |
| MP05B04 | 26.3** | 2.4** | 11.0** | N,A. | N,A. | — |
| MP05G04 | 7.6* | 7.6* | 1.0* | N,A. | N,A. | — |
| MP05G05 | 6.6* | 4.3* | 1.5* | N,A. | N,A. | — |
| MP05H05 j) | 20.2* | 20.7* | 1.0* | N,A. | N,A. | — |
| MP05G06 | 2.4* | 1.7* | 1.4* | N,A. | N,A. | — |

Binders specific to membrane bound mesothelin are marked *,
binders that recognize both the membrane bound and the soluble 5 form are marked **.
N,A.—Not assayed.

TABLE 8

Screening overview table

| Animal | Master library | Master plate ID | # binders to CHO-mesothelin | # specific binders to membrane bound mesothelin | # binders to membrane bound mesothelin and soluble mesothelin | Binders % | Specific binders to membrane bound mesothelin % |
|---|---|---|---|---|---|---|---|
| MM1 | M003κ | FJ1212MP01 | 14 | 13 | 1 | 14.6 | 92.9 |
| MM2 | M004κ | FJ1212MP02 | 66 | 63 | 3 | 68.8 | 95.5 |
| MM3 | M005κ | FJ1212MP03 | 40 | 29 | 11 | 41.7 | 72.5 |
| MM4 | M006κ | FJ1212MP04 | 9 | 9 | 0 | 9.4 | 100.0 |
| MM5 | M007κ | FJ1212MP05 | 9 | 7 | 2 | 9.4 | 77.8 |

CONCLUSIONS

Five Fab libraries were constructed from five mice immunized with P815 cells expressing the membrane bound mesothelin receptor after induced tolerance to the soluble mesothelin receptor. The libraries were subjected to two rounds of selection, first on CHO mesothelin expressing cells and second on P815 mesothelin expressing cells vs the wild type. Five master plates were generated from the round II selection outputs and periplasmic extracts containing soluble Fabs were produced. Of the five master plates 138 clones were confirmed as binders of which 17 showed binding to both forms of the mesothelin receptor and 121 showed specific binding to the membrane bound mesothelin receptor.

This work shows that the combination of a specific immunization protocol to induce tolerance to the soluble receptor and phage display based selections on whole cells allowed the identification of a diverse panel of mouse Fabs with different specificities for the mesothelin receptor, and in particular the selection of Fabs with specific binding to the membrane bound mesothelin receptor.

The invention claimed is:

1. A method of generating an antibody which can discriminate between the membrane bound form of a cell surface protein and the soluble (shed) form of the same cell surface protein by recognizing a difference in conformation between the membrane bound form and the soluble form of the same cell surface protein, the antibody binds to a conformational epitope found entirely in the membrane bound form of the same cell surface protein having 100% sequence identity to the soluble form of the same cell surface protein, the method comprising:
    (i) immunizing an animal with the soluble form of the cell surface protein;
    (ii) administering to the animal a chemotherapeutic agent which selectively kills rapidly dividing B cells;
    (iii) immunizing the animal with whole cells expressing the membrane bound form of the same cell surface protein;
    (iv) screening hybridomas or an antibody library for a candidate antibody which binds to the conformational epitope in the membrane bound form of the same cell surface protein but does not bind to the soluble form of the same cell surface protein; and
    (v) isolating the antibody that binds to the conformational epitope in the membrane bound form of the same cell surface protein but does not bind to the soluble form of the same cell surface protein.

2. The method of claim 1, wherein the same cell surface protein is a tumor associated antigen or an antigen associated with a sub-type of T-cells.

3. The method of claim 1, wherein the chemotherapeutic agent is cyclophosphamide.

4. The method of claim 1, wherein steps (i) and (ii) are repeated at least once.

5. The method of claim 1, wherein said animal is a mouse.

6. The method of claim 1, further comprising
    manufacturing or producing the antibody; and
    optionally formulating the antibody with at least one pharmaceutically acceptable carrier or excipient.

7. The method of claim 1, further comprising
manufacturing or producing an antigen binding fragment of the antibody or an immunoconjugate of the antibody; and
formulating the antigen binding fragment or the immunoconjugate with at least one pharmaceutically acceptable carrier or excipient.

* * * * *